(12) United States Patent
David et al.

(10) Patent No.: US 8,025,669 B1
(45) Date of Patent: Sep. 27, 2011

(54) PORTABLE MICRODERM ABRASION DEVICE

(75) Inventors: Jonathan Edward David, Rolling Hills, CA (US); Dale W. Bolen, Rolling Hills, CA (US)

(73) Assignee: Biorenew Labs, LLC, Rolling Hills, CA (US)

( * ) Notice: Subject to any disclaimer, the term of this patent is extended or adjusted under 35 U.S.C. 154(b) by 1058 days.

(21) Appl. No.: 11/490,456

(22) Filed: Jul. 19, 2006

Related U.S. Application Data

(60) Provisional application No. 60/701,572, filed on Jul. 22, 2005.

(51) Int. Cl.
*A61B 17/50* (2006.01)
(52) U.S. Cl. .......................................... 606/131; 451/87
(58) Field of Classification Search .............. 606/131, 606/133; 601/17; 451/2, 90, 99, 102, 87, 451/88, 453, 456, 451; 604/290, 289; 15/347, 15/327.5, 344, 352
See application file for complete search history.

(56) References Cited

U.S. PATENT DOCUMENTS

| | | | |
|---|---|---|---|
| 6,039,745 A | | 3/2000 | Di Fiore et al. |
| 6,250,996 B1 * | | 6/2001 | Metcalf et al. ................... 451/87 |
| 6,540,757 B1 | | 4/2003 | Hruska et al. |
| 6,706,033 B1 * | | 3/2004 | Martinez et al. ............... 604/523 |
| 7,070,488 B2 * | | 7/2006 | Suissa et al. ..................... 451/87 |
| 2001/0023351 A1 * | | 9/2001 | Eilers et al. ..................... 606/131 |
| 2003/0093089 A1 * | | 5/2003 | Greenberg ...................... 606/131 |
| 2004/0243149 A1 | | 12/2004 | Lee, Jr. |
| 2005/0245180 A1 | | 11/2005 | Suissa et al. |

FOREIGN PATENT DOCUMENTS

| | | |
|---|---|---|
| FR | 2845885 | 10/2002 |
| FR | 2845886 | 10/2002 |
| WO | WO 2004/037098 | 5/2004 |
| WO | WO 2004037098 A1 * | 5/2004 |

* cited by examiner

*Primary Examiner* — Anhtuan Nguyen
*Assistant Examiner* — Tin Nguyen
(74) *Attorney, Agent, or Firm* — Cislo & Thomas, LLP

(57) ABSTRACT

A portable microderm abrasion device is comprised of a hollow housing containing an electric motor that operates an air pump having air suction and air exhaust ports. A hollow, disposable exfoliation grit supply cartridge is removably located within an upper bay, while a separate hollow, disposable waste collection cartridge is also located within a lower bay in the housing directly beneath the grit supply cartridge. The two cartridges are separately removable from the housing. Grit from the supply cartridge is mixed with air drawn by a vacuum created by the air pump into a grit entrainment duct located within the waste collection cartridge and carried to a movable wand. A particulate filter located in the waste collection cartridge allows air, but prevents solid waste material, from being discharged to ambient atmosphere. Safety features include a timer and/or a motion sensor to reduce or cut off vacuum in the line if the grit dispensing and retrieval tip of the wand remains in a static condition or exerts a vacuum for too long a period of time upon the skin of the subject.

20 Claims, 22 Drawing Sheets

PORTABLE MICRODERM ABRASION DEVICE

The present application claims the benefit of Provisional Patent Application Ser. No. 60/701,572 filed Jul. 22, 2005.

BACKGROUND OF THE INVENTION

1. Field of the Invention

The present invention relates a skin treatment system in which a mechanical device is used to apply light abrasive material to the skin of a person undergoing treatment. The process is often termed microderm abrasion, but is also referred to by other terms such as, skin peeling and exfoliation.

2. Description of the Prior Art

Microderm abrasion is a procedure that may be performed, for example, to exfoliate layers of a person's skin for cosmetic or other reasons. During the procedure very small particulate crystals having light abrasive characteristics are supplied in a first container. A vacuum air flow is then used to entrain the crystals in air and apply them onto the skin of a person through an application wand. As the wand sprays crystals against the skin of the subject, the crystals, along with dead skin cells are then vacuumed by the wand and returned through a separate hose and deposited in a second container to be discarded. The operator must replace or refill the first container when it runs out of crystals, and also empty or discard the second container when it becomes full.

Conventional microderm abrasion devices are described for example, in U.S. Publication No. 2005/0245180 published Nov. 3, 2005, U.S. Publication No. 2004/0243149 published Dec. 2, 2004, PCT Application No. PCT/FR2003/003125 published by WIPO as WO 2004/037098 on May 6, 2004, French Patent No. 2,845,885 filed Oct. 21, 2002 and French Patent No. 2,845,886 also filed Oct. 21, 2002.

While conventional microderm abrasion devices do perform their intended function, they present considerable drawbacks. One problem of such conventional systems is that, while the crystals are being strayed against the skin, the operator must keep the wand in constant motion to avoid over-treatment on a specific area. This is a safety issue that makes the treatment depth very operator dependent. If the operator applies the wand in such a manner that crystals are sprayed against the same area of the skin for too long a time, skin damage can occur. If the operator does not spray the crystals long enough, exfoliation is inadequate.

Another problem with conventional microderm abrasion devices is that they are highly susceptible to clogging. The crystals must be entrained in air in order to be sprayed onto the skin of a subject. However, due to the narrow and convoluted passageways through which the crystals pass, there is a high incidence of clogging of the crystals in the line. This is usually due to clumping of crystals or the presence of oversized debris in the crystals. Once clogging occurs it can be a difficult, expensive and time consuming process to unclog the system.

A further disadvantage of conventional microderm abrasion systems is that the manufacture and repair of these machines and the provision supply parts is expensive. When clogging occurs it is often difficult to locate and clear the obstruction. A lay person is often unable to repair the machine. Therefore, the machine must be sent back to the manufacturer for repair. Even in those devices in which the crystal supply container is disposable, it is often difficult to access and replace by a lay person.

A further disadvantage of conventional system is that, when a consumer purchases a microderm abrasion system, the purchaser will often elect to purchase replacement crystals from a supplier other than the original equipment manufacturer. This causes a loss of revenue to the manufacturer, and also contributes to product malfunctions, which are then blamed upon the manufacturer.

SUMMARY OF THE INVENTION

The present invention employs a uniquely designed microderm abrasion device that utilizes a new conception in the interaction of components that alleviates the inherent problems in the prior art. Some of the unique aspects of the portable microderm abrasion device of the invention is that it is safer to use than conventional microderm abrasion devices. The device of the invention includes safety features that prevent or reduce the quantity of crystals that impact the skin of a subject for more than a predetermined duration of time or with a certain amount of force.

Another improvement of the invention is that the grit supply cartridge is a disposable unit that is easily accessible to a user. As a consequence, it is considerably easier for a user to first try to clear clogs if they occur at the grit discharge opening of the grit supply cartridge. Furthermore, if a clog cannot be cleared, then the supply unit can be discarded and replaced with minimal time, effort, and economic loss.

A further important feature of the invention is that the grit pickup area where grit is entrained with air is fabricated as a part of the waste collection cartridge, which is also disposable. As a consequence, the cost of manufacture of the device is reduced since no separate second entrainment mechanism is required beyond that embodied in the disposable grit supply and waste collection cartridges.

A further advantage of the invention is that the grit supply cartridge and waste collection cartridges are separate units. They are detachable from the housing independently of each other, but fit together in the housing in a compact, cooperative fashion. Both the grit supply cartridge and the waste collection cartridge are configured with unique, interactive couplings to each other and to the housing of the device so that a user is much more likely to purchase refill grit supply and waste collection cartridges from the original manufacturer of the device.

The primary object of the present invention is to provide a safer, more reliable, and economical device for creating microabrasions on the skin, as well as such a device which is easier to operate and service than conventional microderm abrasion machines.

The microderm abrasion device of the invention preferably is provided with safety features that are built in and which are not present in prior art devices. Serious complications can arise from the over treatment of the skin of a subject with conventional microderm abrasion systems and other types of skin treatments that use a stream of abrasive material to abrade the skin. Presently an operator of a conventional device can easily over treat skin by allowing the abrasive stream to impact the same area of the skin for an excessive length of time. As a consequence, impacting, abrasive particles dig too deeply into the skin, thereby causing pain and creating discoloration.

The preferred embodiments of the invention incorporate several alternative mechanisms that prevent or reduce the likelihood of excessive skin abrasion. Possible safety mechanisms include, but are not limited to, detection and control arrangements that automatically halt treatment if a possibility of over treatment is detected, or a warning system to alert the operator of an impending unsafe condition. The warning system can be audible, visual, or tactile. Treatments can be interrupted for safety reasons by reducing or relieving the suction entirely, interrupting the flow of the abrasive media, or shutting down electrical power to the vacuum pump until the threat of over treatment is reduced. Another way of reducing risk is to reduce the flow rate or density of the abrasive material.

The system of the present invention can detect the existence of a threat by measuring the sustained time period during which suction is applied to the skin (e.g., the wand has not been lifted from the skin). Alternatively, movement of the treatment wand can be monitored to detect when it has remained static too long at a specific skin location and thus should be moved to a new, untreated area. If the wand remains static for too long a period, suction can be halted, reduced, or the intensity of treatment can otherwise be diminished. The intensity of treatment can be reduced or halted entirely through a variety of mechanical, electrical, or fluid operating mechanisms.

In one broad aspect the present invention may be considered to be a portable microderm abrasion device comprising a hollow housing, an electrically operated motor, an air pump, a hollow exfoliation grit supply cartridge, a hollow exfoliation waste collection cartridge, a movable wand, grit supply and waste return tubes, a grit filter, and an exhaust tube. The electrically operated motor is located within the housing. The air pump is also located within the housing and is operated by the motor. The air pump has an air suction port and an air exhaust port. The hollow exfoliation grit supply cartridge is removably located within the housing and has a grit discharge opening.

The hollow exfoliation waste collection cartridge is separate from the grit supply cartridge. It is also located within a receiving bay in the housing. The grit supply cartridge is removable from the housing independently of the waste collection cartridge. The waste collection cartridge has a grit supply coupling, an air intake port, a wand supply port, a wand return port, and an air discharge port. The grit discharge opening of the grit supply cartridge resides in communication with the grit supply coupling.

A grit entrainment duct defined within the waste collection cartridge leads from the air intake port and from the supply coupling and to the wand supply port. The movable wand terminates in a grit dispensing and retrieval tip remote from the housing.

Separate exfoliation grit supply and waste return tubes lead to the grit dispensing and retrieval tip. The exfoliation grit supply tube is coupled between the grit dispensing and retrieval tip and the wand supply port. The waste return tube is coupled between the grit dispensing and retrieval tip and the wand return port.

A grit filter is located in the waste collection cartridge and is interposed between the wand return port and the air discharge port. The grit filter excludes particulate matter, primarily grit and dead skin, from the air discharge port. The air exhaust tube is connected between the air discharge port in the waste collection cartridge and the air suction port in the air pump.

In another broad aspect the invention may be considered to be an improvement in a microderm abrasion apparatus having a housing containing an electrical motor, a pneumatic vacuum pump, a wand movable relative to the housing and having a grit dispensing and recovery tip. According to the improvement of the invention a disposable abrasive waste recovery cartridge is seated in a bay in the housing, a separate disposable grit supply cartridge is seating in a different bay in the housing and also upon the disposable abrasive waste recovery cartridge. The grit supply cartridge and the waste recovery cartridge are both separately detachable from the housing.

In preferred embodiments the system includes a vacuum sensor, a timer coupled to the vacuum sensor for measuring the duration of continuous application of vacuum suction by the vacuum pump upon the grit dispensing and recovery tip, and some means for interrupting the supply of grit to the grit dispensing and recovery tip in response to signals from the timer. One means for accomplishing this result is a vacuum interruption valve located between disposable grit supply cartridge and the vacuum pump.

In another aspect of the invention the conventional operating components of a microderm abrasion device are combined with a vacuum sensor, a timer coupled to the vacuum sensor, and a flow check device connected to the timer and to the grit supply cartridge to block the flow of grit therefrom upon duration of the vacuum for a predetermined time interval.

In still another aspect of the invention the conventional components of the microderm abrasion apparatus are combined with a motion sensor in the grit dispensing and recovery tip and a timer for limiting the duration of continuous application of suction by the vacuum pump at the grit dispensing and recovery tip upon detection from the motion sensor of a static condition of the grit dispensing and recovery tip for a predetermined duration of time.

The microderm abrasion device of the invention is more reliable and easier to service than conventional systems. The portable unit of the present invention helps alleviate the service, time, and cost issues that otherwise result from clogging of the grit in the unit by forming the seating cavities for both the grit supply cartridge and the waste collection cartridge as bays on an outside wall of the microderm abrasion unit housing. The grit supply cartridge is interconnected with the waste collection cartridge so that both are proximately located and easily accessible, but are separately detachable from the housing.

If clogging in the unit does occur, the operator has extremely easy access to the entrainment passageway, since it is incorporated into the structure of the waste disposal cartridge which can be easily detached from the housing. By locating the two cartridges together such that they fit detachably into configured bays or recesses in the housing designed to snugly receive them, the waste collection cartridge can be easily detached and removed from the housing once it is full of waste material. Similarly, the grit supply cartridge can be easily detached and removed from the housing for refilling or replacement without necessarily detaching the waste collection cartridge. A clean grit supply cartridge can then be easily inserted into its receiving bay cavity in the housing.

Furthermore, since significant components of the supply and return passageways are incorporated into the disposable waste collection cartridge, the probability of clogging from accumulated oils and debris is alleviated. The passageways where such clogging is likely to occur are part of the disposable grit supply and waste collection cartridge units. Unclogging of these passageways is considerably easier, since the units containing them, namely the waste collection cartridge and the grit supply cartridge are easily detachable from the housing to allow much greater access to many of the important passageways. Moreover, if the user is unable to unclog the system, the waste canister which includes the entrainment passageway, can be discarded and a new one inserted. As a consequence, there is less likelihood of necessity for return of the machine to the manufacturer for repair.

A further advantage of integrating the grit entrainment passageway into part of another disposable component of the system is that money is saved in the manufacturing process. Because the entrainment passageway is built into the structure of the waste canister as an internal component, fabrication of a separate part is unnecessary. This aspect of the invention results in a more reliable, easier to service system and one which is more economical to manufacture than conventional systems.

Due to the unique design and interengagement of the grit supply cartridge and the waste collection cartridge there is an inducement for operators to obtain both used collection cartridges and new supply cartridges from the equipment manufacturer. This is of benefit to the manufacturer, both due to the sales that result and also the reduction of service problems that can otherwise occur by the use of components and grit materials for which the machine is not designed.

The invention may be described with greater clarity and particularity by reference to the accompanying drawings.

DESCRIPTION OF THE EMBODIMENTS

Figure 1:
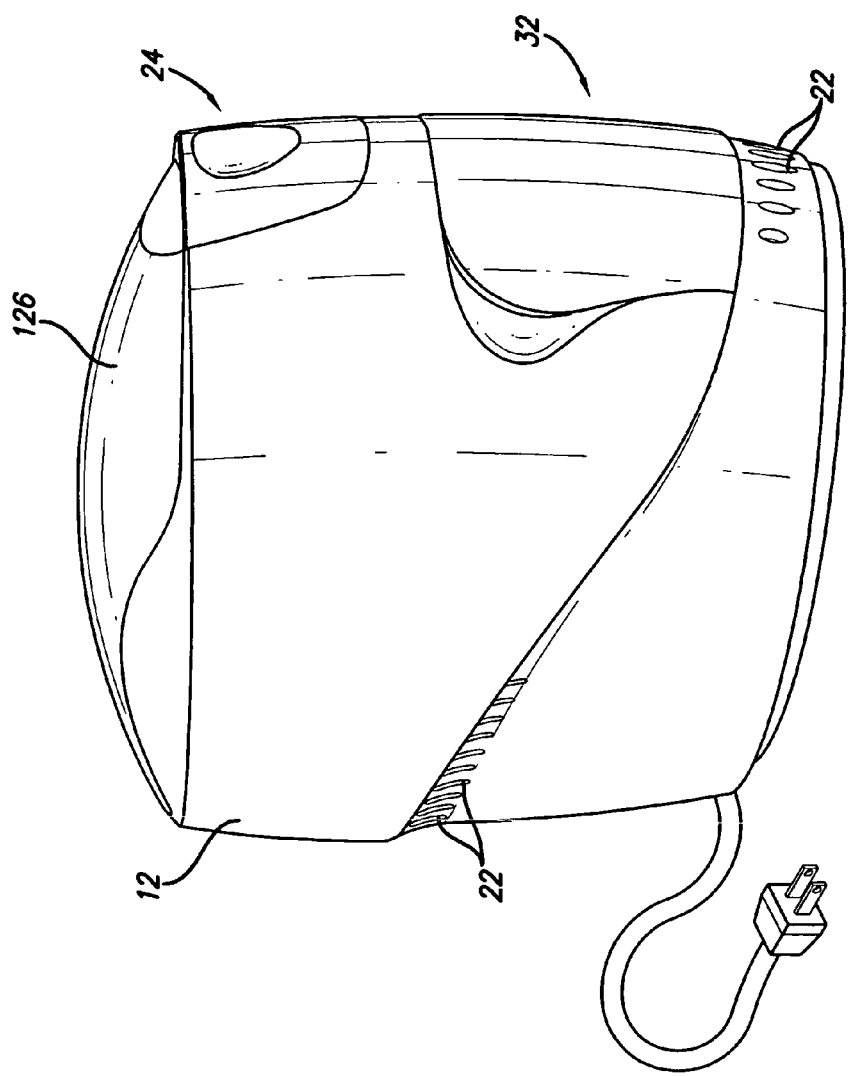
FIG. 1 is a perspective view of a portable microderm abrasion apparatus constructed according to the present invention.
Figure 2:
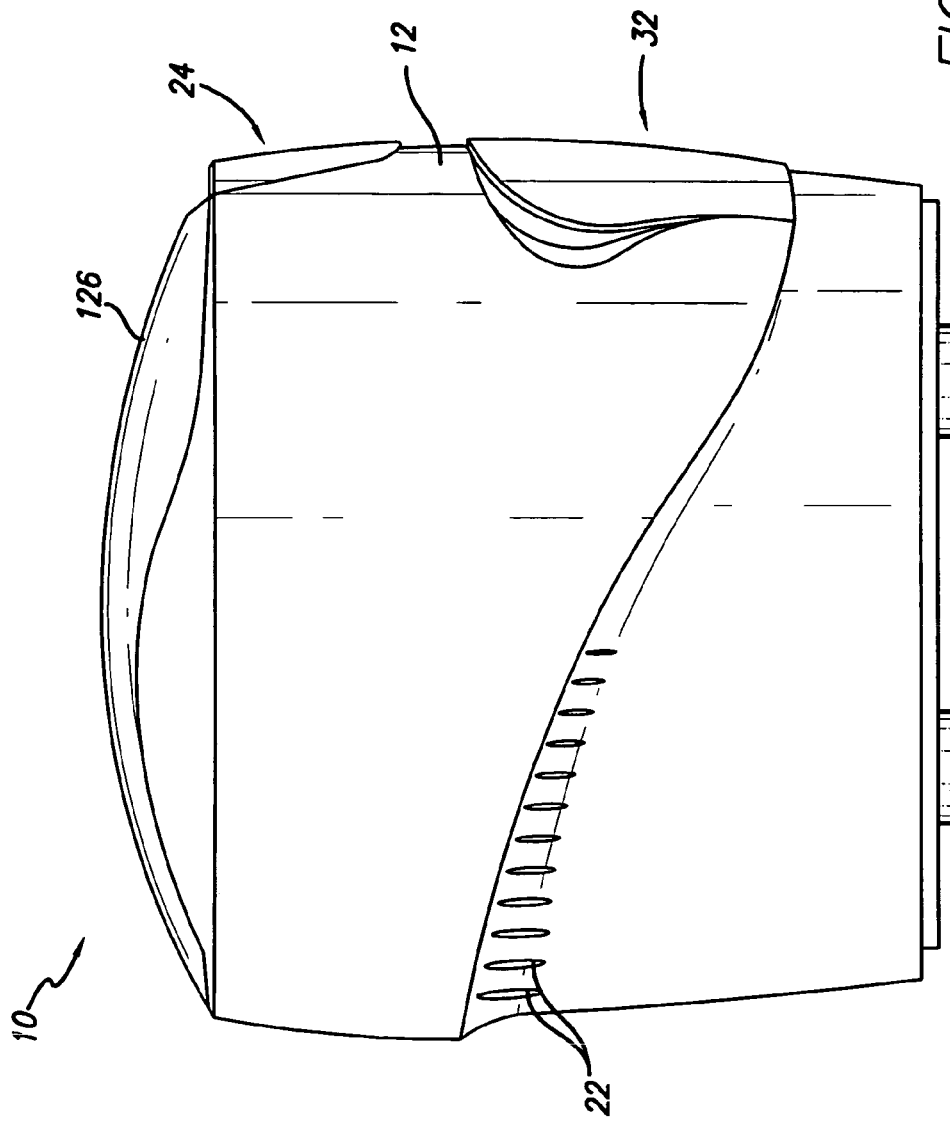
FIG. 2 is a side elevational view thereof.
Figure 4:
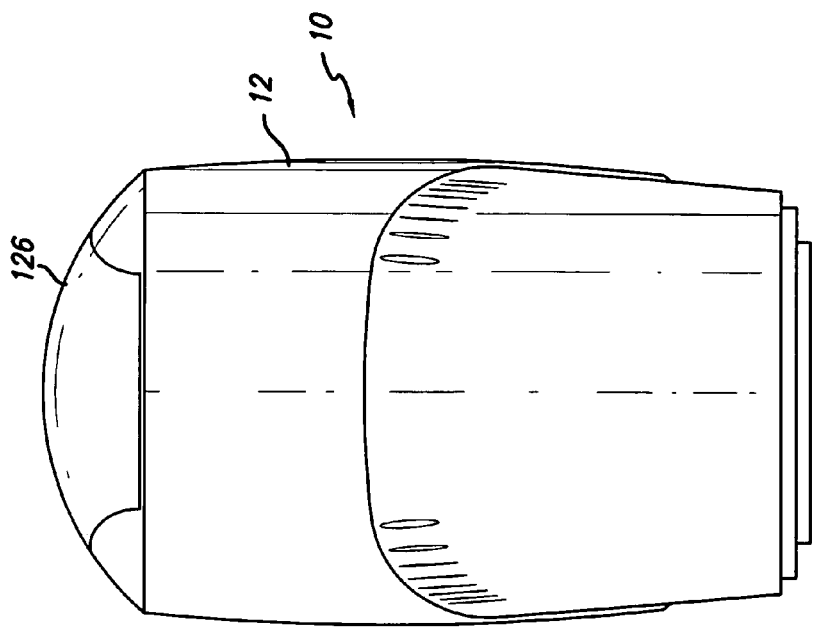
FIG. 4 is a rear elevational view thereof.
Figure 3:
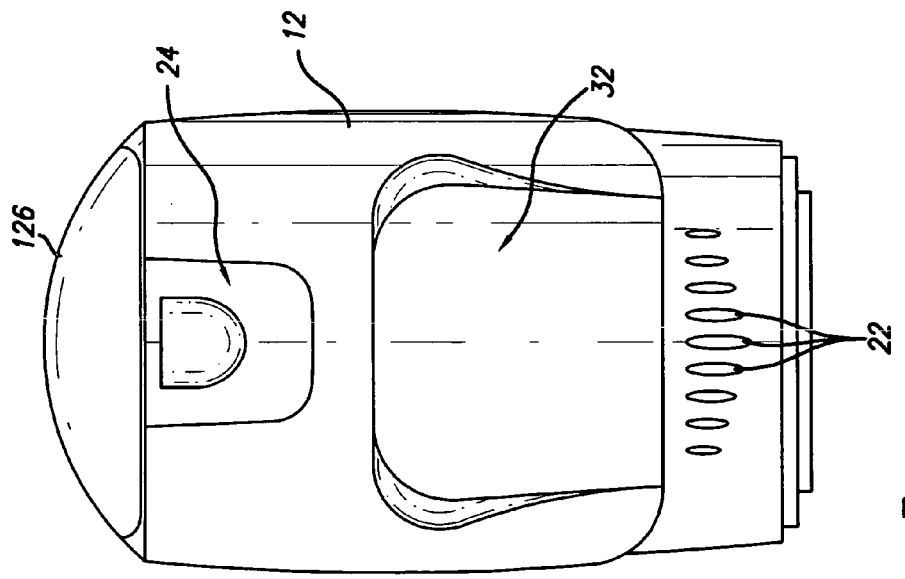
FIG. 3 is a front elevational view thereof.
Figure 5:
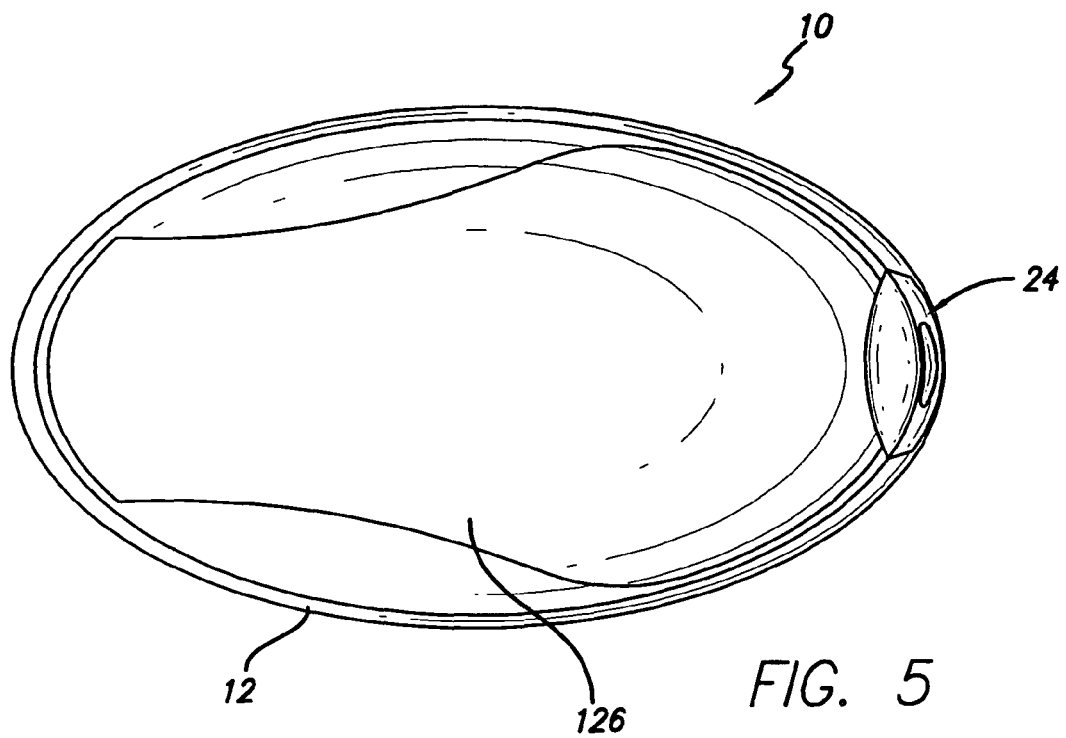
FIG. 5 is a top plan view thereof.
Figure 6:
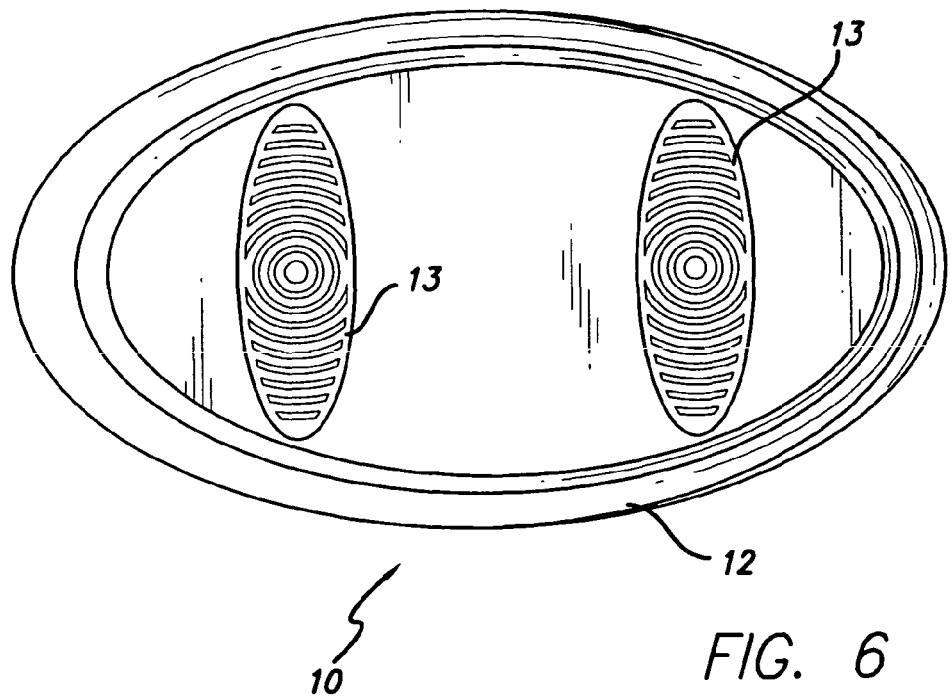
FIG. 6 is a bottom plan view thereof.
Figure 10:
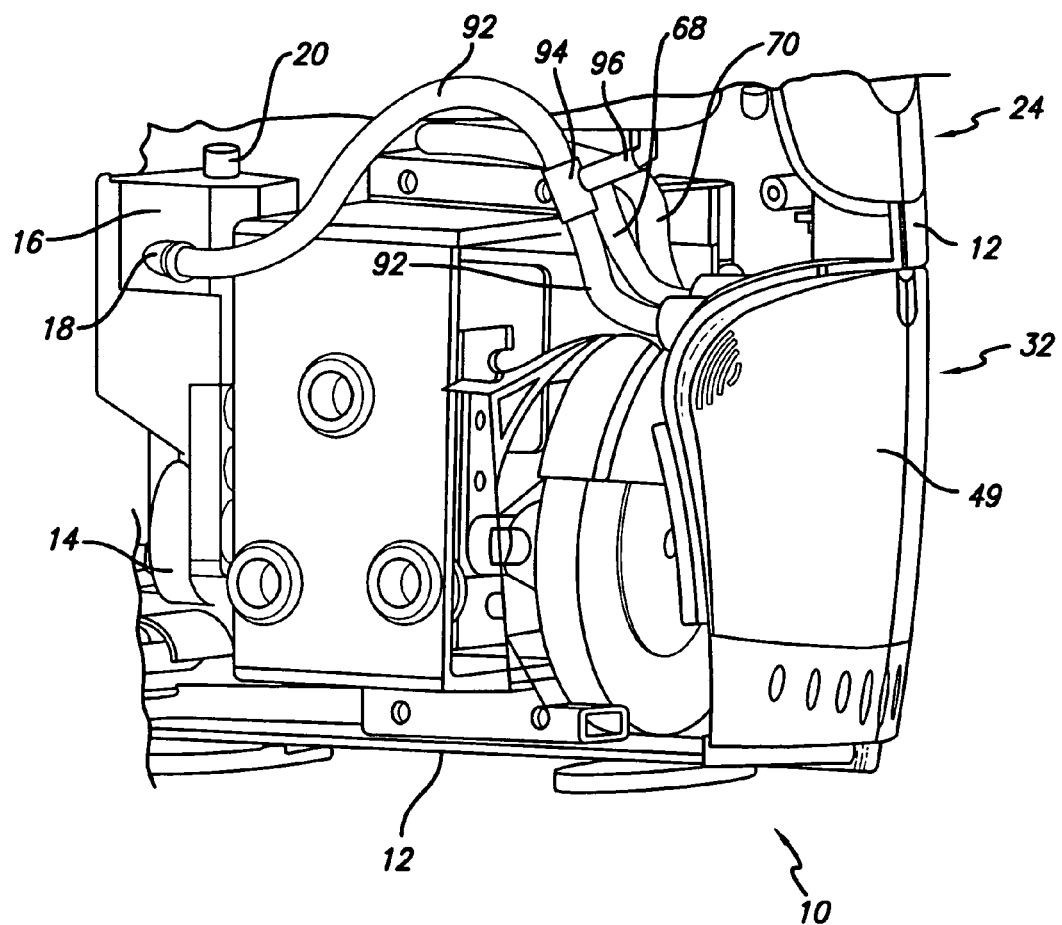
FIG. 10 is an enlarged side elevational detail showing the interior of the housing with a portion of the exterior side wall thereof removed to allow illustration of internal components.

FIGS. 1, 2, and 10, for example, illustrate a portable microderm abrasion device indicated generally at 10 that is comprised of a hollow casing or housing 12 with a lid 126 on its top and supporting rubber feet 13 on its bottom. Within the housing 12 there is an electrically operated motor 14, and an air pump 16 operated by the motor 14. The electric motor 14 is a conventional one hundred twenty volt, alternating current motor, while the air pump 16 is also conventional. The motor 14 and the air pump 16 are partially visible in the broken away view of FIG. 10. The air pump 16 has an air suction port 18 and an air exhaust port 20 that exhausts air into the hollow interior of the casing 12. Air is discharged from the interior of the housing 12 through vent openings 22.

Figure 14:
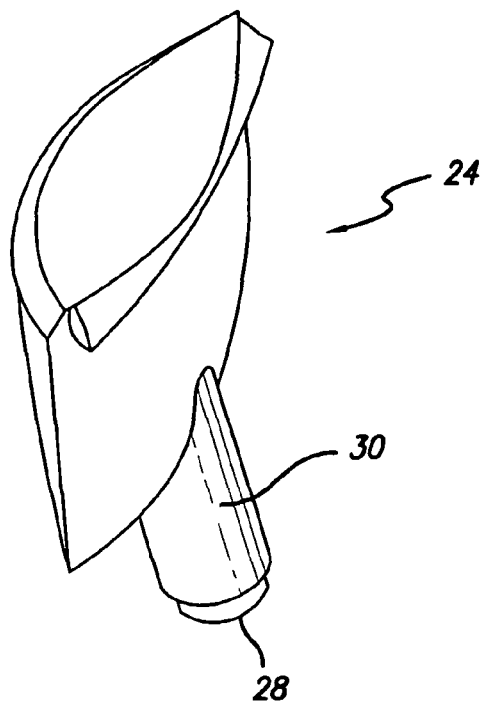
FIG. 14 is a perspective view of the grit supply cartridge of the invention, shown in isolation.
Figure 19:
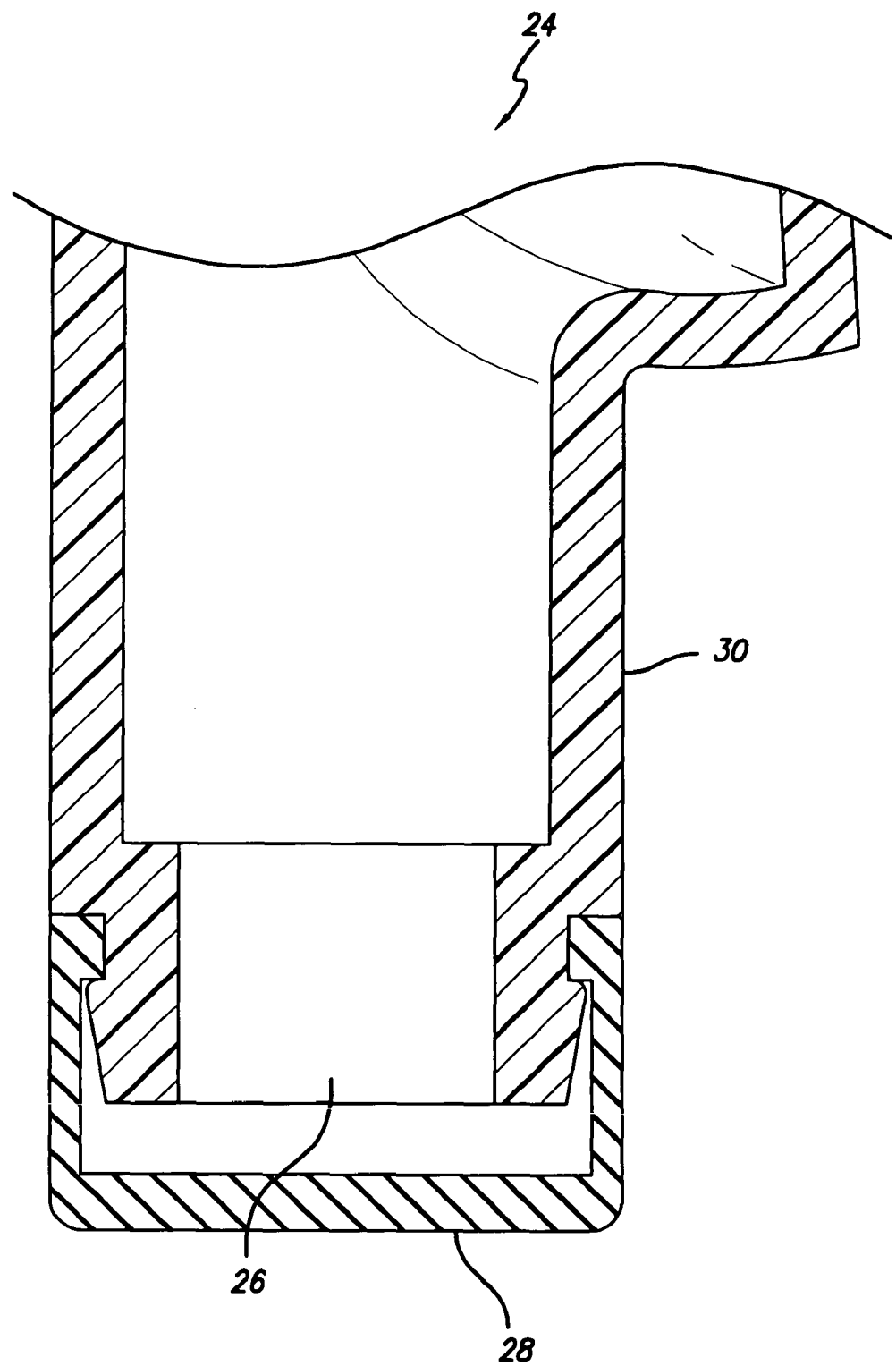
FIG. 19 is a sectional elevational detail showing the grit supply cartridge neck and grit discharge opening in isolation.

The microderm abrasion unit 10 has a hollow exfoliation grit supply cartridge 24 that is removably located within the housing 12 and which has a grit discharge opening 26, visible in FIG. 19. The discharge opening 26 is covered by a puncturable septum 28, also shown in FIG. 19. The grit supply cartridge 24 initially contains a supply of small, granular microderm abrasion grit particles, which are typically crystalline in nature. These grit particles are referred to as microderm abrasion crystals, in the trade. The grit supply cartridge 24 has upper and lower ends and is configured with a narrow grit discharge neck 30 terminating in the grit discharge opening 26. The narrow neck 30 is located in the lower end of the grit supply cartridge 24. At the lower end of the grit supply cartridge 24 the hollow, cylindrical neck 30 that leads to the grit discharge opening 26 and is covered by the puncturable septum 28, as shown in FIGS. 14 and 19.

The portable microderm abrasion device 10 also has a hollow exfoliation waste collection cartridge 32 that is separate from the grit supply cartridge 24. The waste collection cartridge 32 is also located within the housing 12. The waste collection cartridge 32 is removable from the housing 12 separately from the grit supply cartridge 24.

The waste collection cartridge 32 has an upper end 34 and a lower end 36, and an inside wall 38 therebetween facing the housing 12. At its front the housing 12 has an outer surface with an exposed waste collection cartridge bay indicated at 40 in FIG. 16. As is evident from FIGS. 1, 12, and 16, the separate enclosed waste collection cartridge bay 40 is contoured to snugly receive and seat the waste collection cartridge 32.

Figure 8:
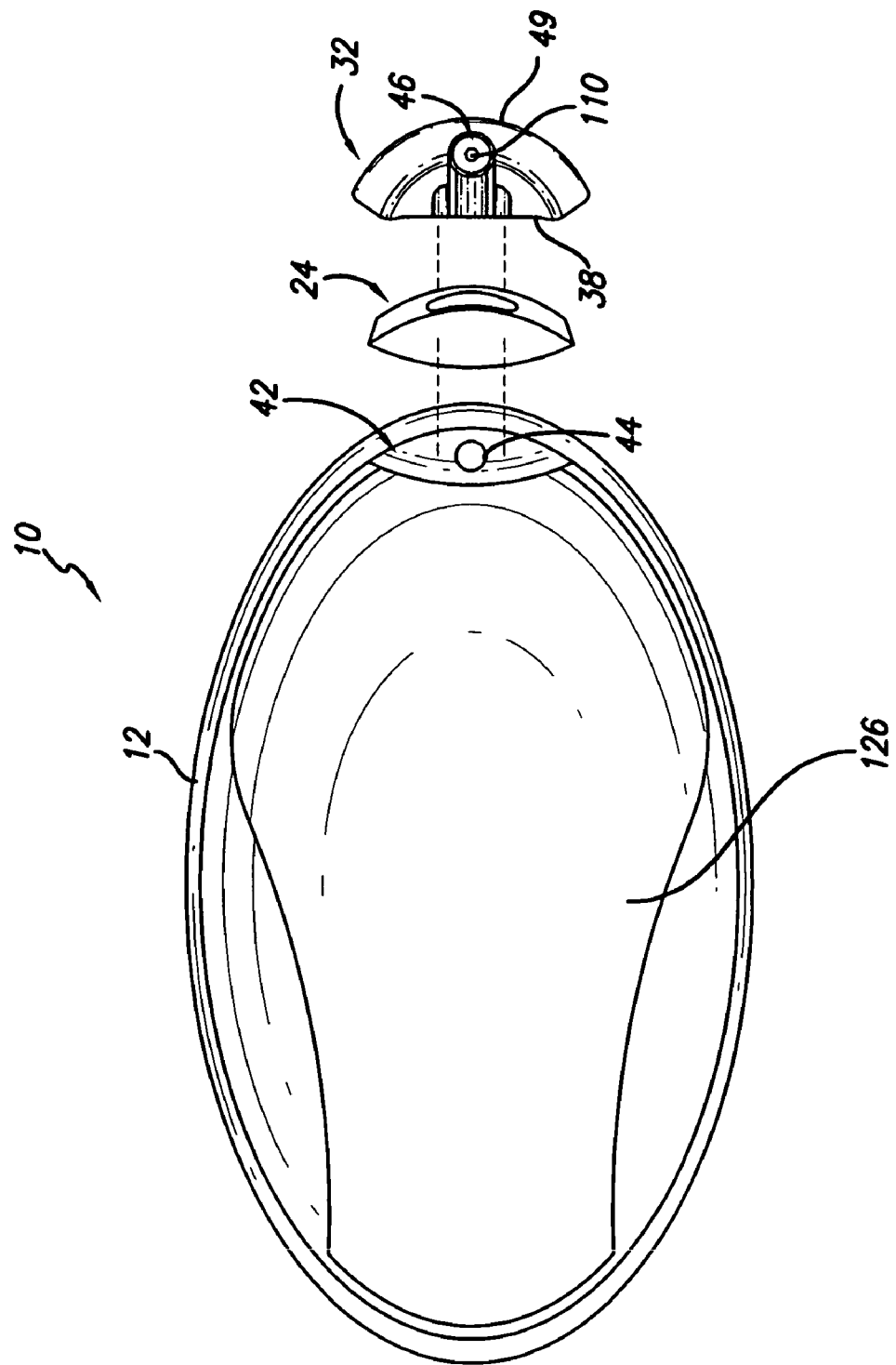
FIG. 8 is a top plan view also showing the components detached as in FIG. 7.
Figure 9:
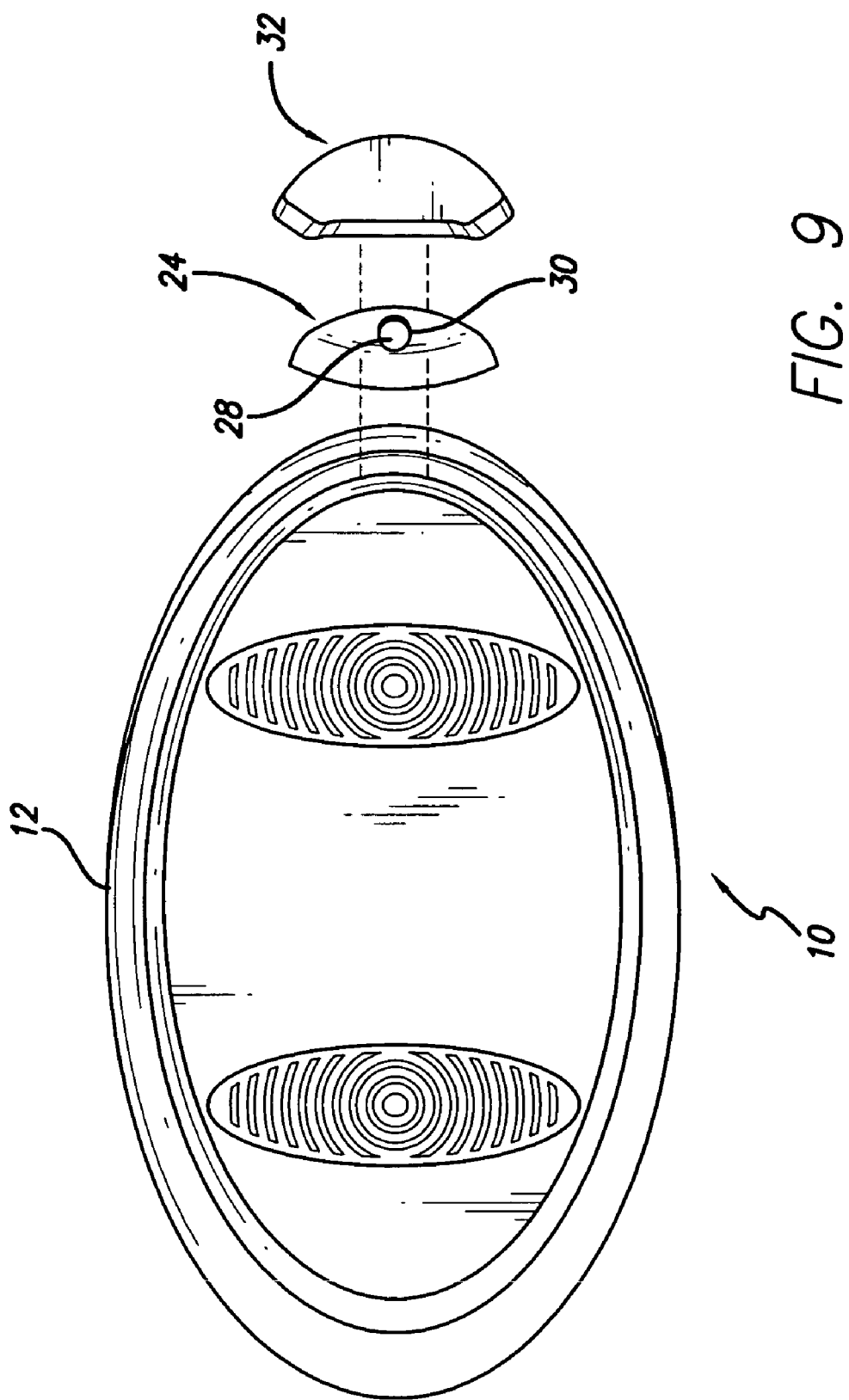
FIG. 9 is a bottom plan view also showing the components thereof detached as in FIG. 7.

Similarly, the front of the housing 12 also defines an open, concave forwardly facing grit supply cartridge bay 42, which is shown exposed in FIG. 8. As is evident in FIGS. 1 and 8, the grit supply cartridge bay 42 snugly receives and seats the grit supply cartridge 24. The grit supply cartridge 24 is detachable from the housing 12 independently of the waste collection cartridge 32. Both the grit supply cartridge 24 and its corresponding seating bay 42 are configured to ensure a secure fit once the waste collection cartridge 32 has been inserted into its seating bay 40 in the housing 12.

Figure 7:
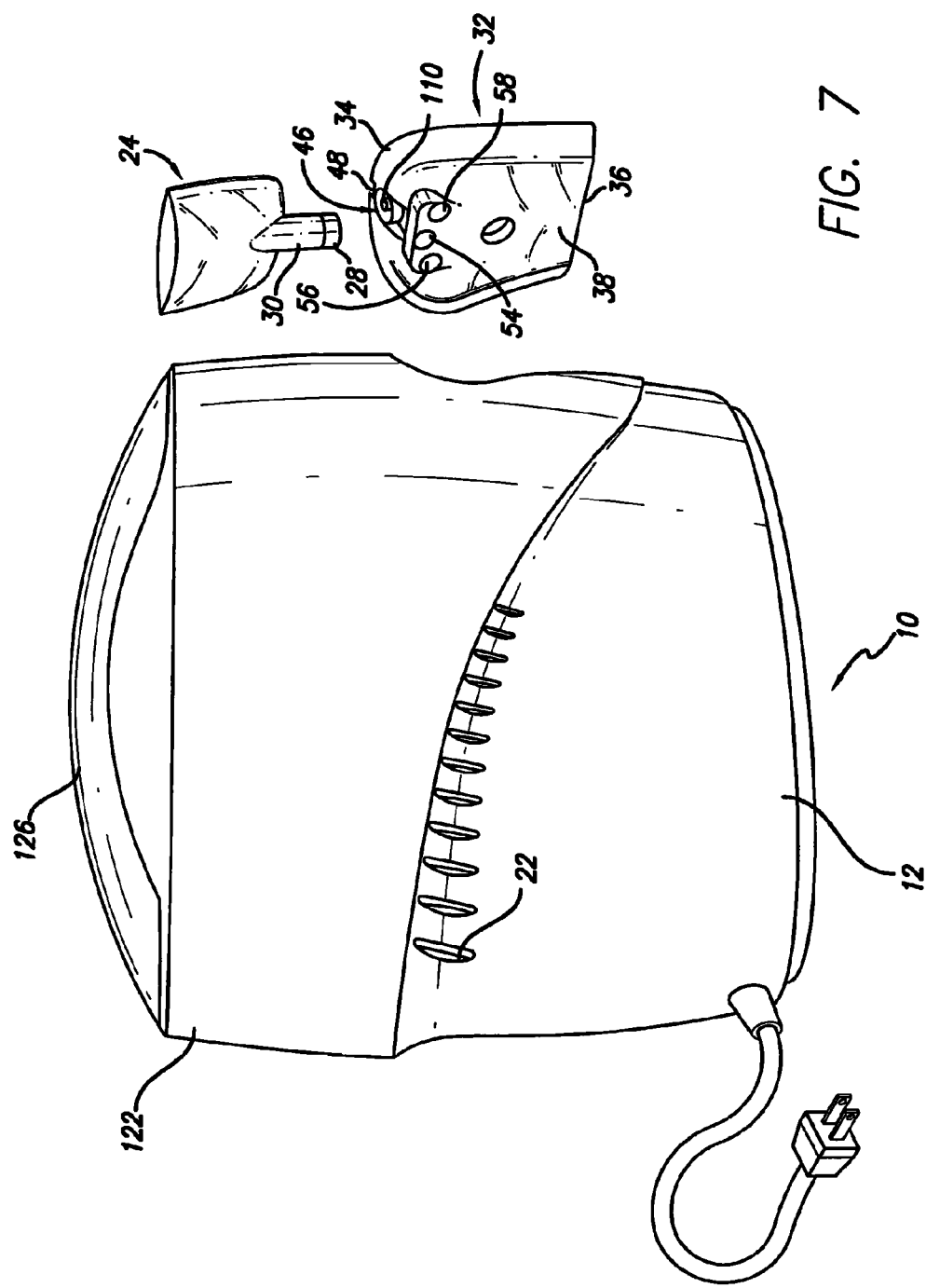
FIG. 7 is an exploded rear perspective view thereof showing both the grit supply cartridge and the waste collection cartridge detached from the housing.
Figure 12:
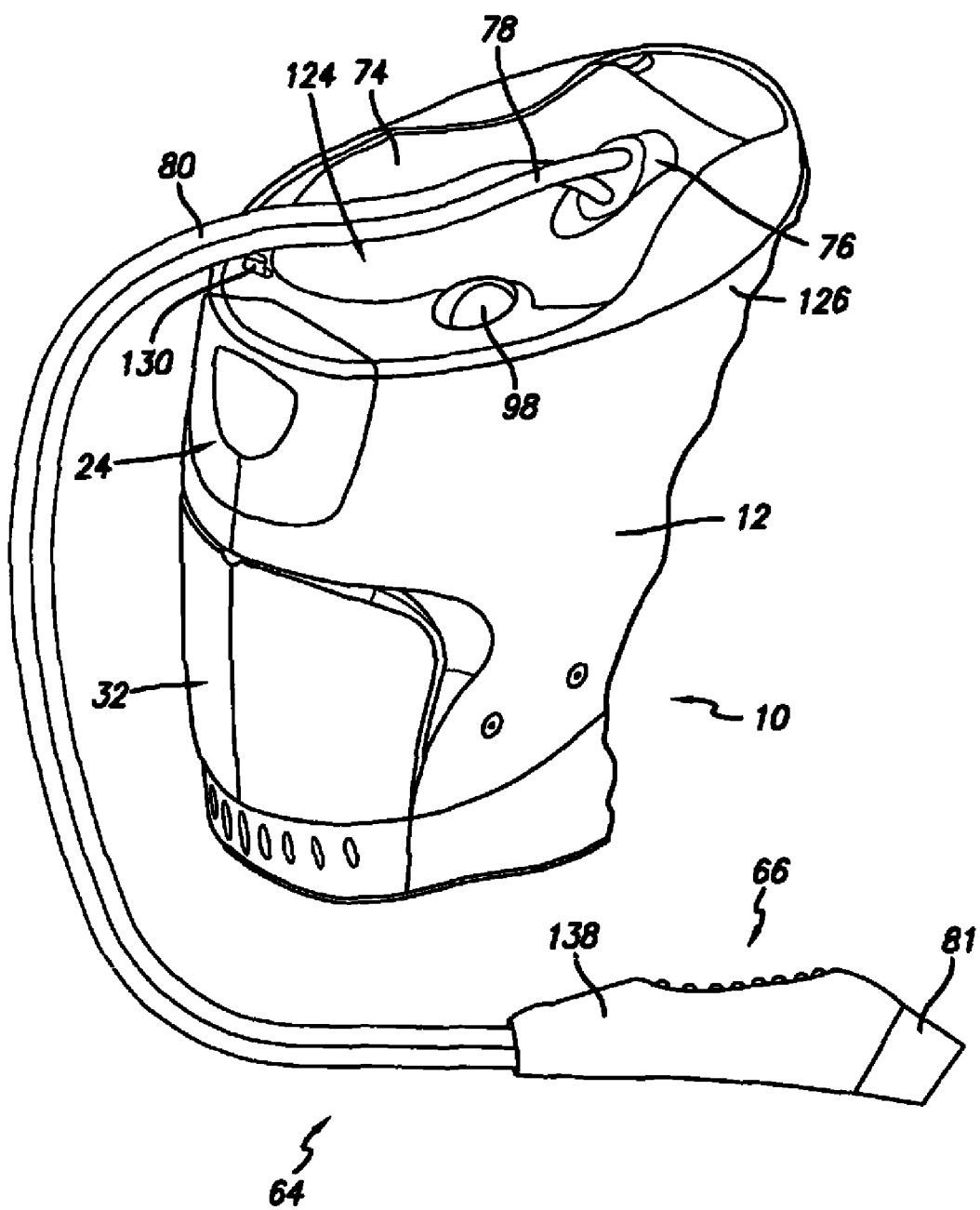
FIG. 12 is a right front perspective detail of a portion of the microderm abrasion unit of the invention showing the wand withdrawn from is storage pocket.

As is evident from FIGS. 1 and 7, both the grit supply cartridge 24 and the waste collection cartridge 32 match the contours of their respective seating bays 42 and 40 formed in the housing 12. FIG. 12 illustrates a more detailed view of the close fitting configuration of the grit supply cartridge 24 and the waste collection cartridge 32 relative to the housing 12.

Figure 18:
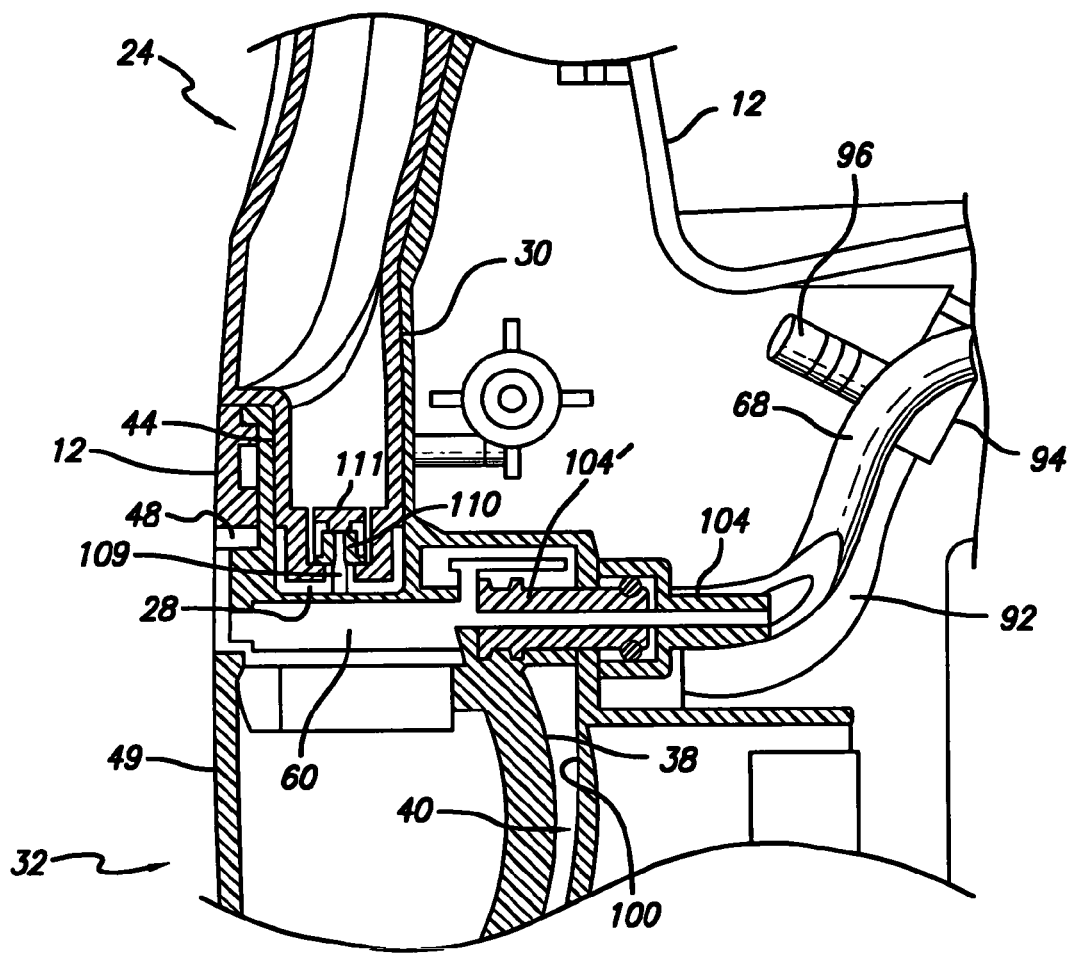
FIG. 18 is a sectional elevational detail within the housing showing the interface between the grit supply cartridge and waste collection cartridge.

As illustrated in FIGS. 8 and 18 an enclosed, cylindrical channel 44 is defined in the housing 12. The channel 44 extends between the grit supply cartridge bay 42 and the waste collection cartridge bay 40 to accommodate communication between the grit discharge opening 26 of the grit supply cartridge 24 and a grit supply coupling 46 defined in the top 34 of the waste collection cartridge 32. Communication between the grit discharge opening 26 and the grit supply coupling 46 exists when the grit supply cartridge 24 and the waste collection cartridge 32 are both seated in their respective cavities 42 and 40.

Figure 15:
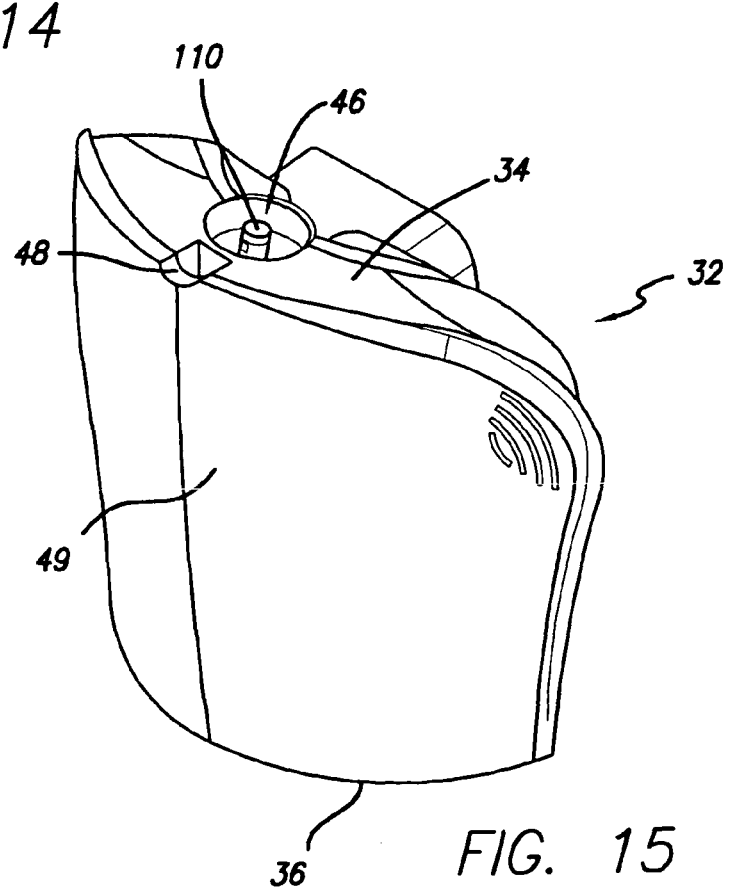
FIG. 15 is a perspective view of the waste collection cartridge of the invention shown in isolation.
Figure 22:
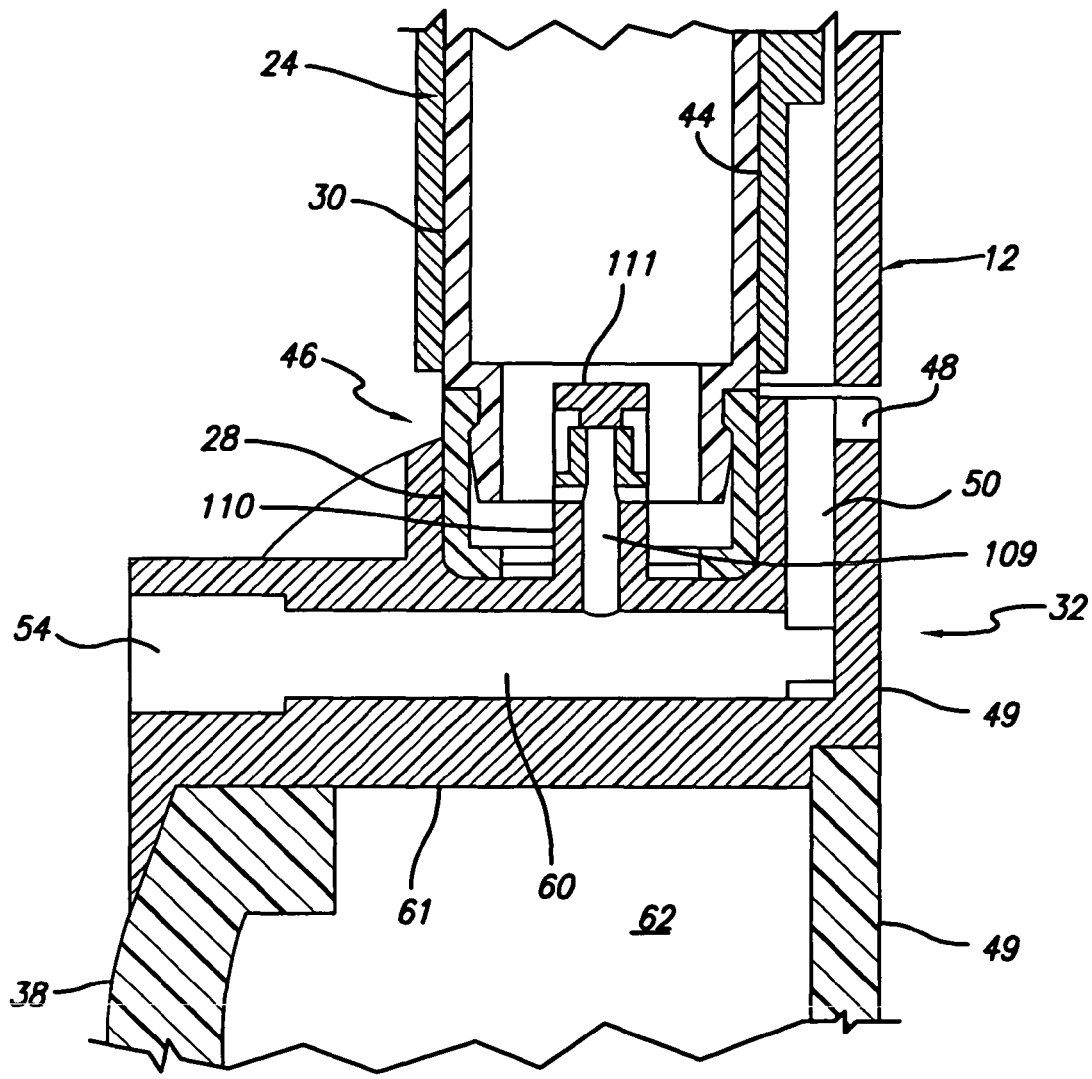
FIG. 22 is a sectional elevational detail illustrating the interconnection between the grit supply cartridge and the waste collection cartridge.

As best illustrated in FIGS. 7, 15, and 22, the waste collection cartridge 32 has, in addition to the grit supply coupling 46, an air intake port 48, which is formed as a small notch in the front of the top 34 of the waste collection cartridge 32, just behind the convex, outwardly facing curved forward wall 49 thereof. The air intake port 48 opens into a short, vertical air channel 50, shown in FIG. 22, that extends downwardly just behind the forwardly facing, convex front wall 49 of the waste collection cartridge 32.

Figure 20:
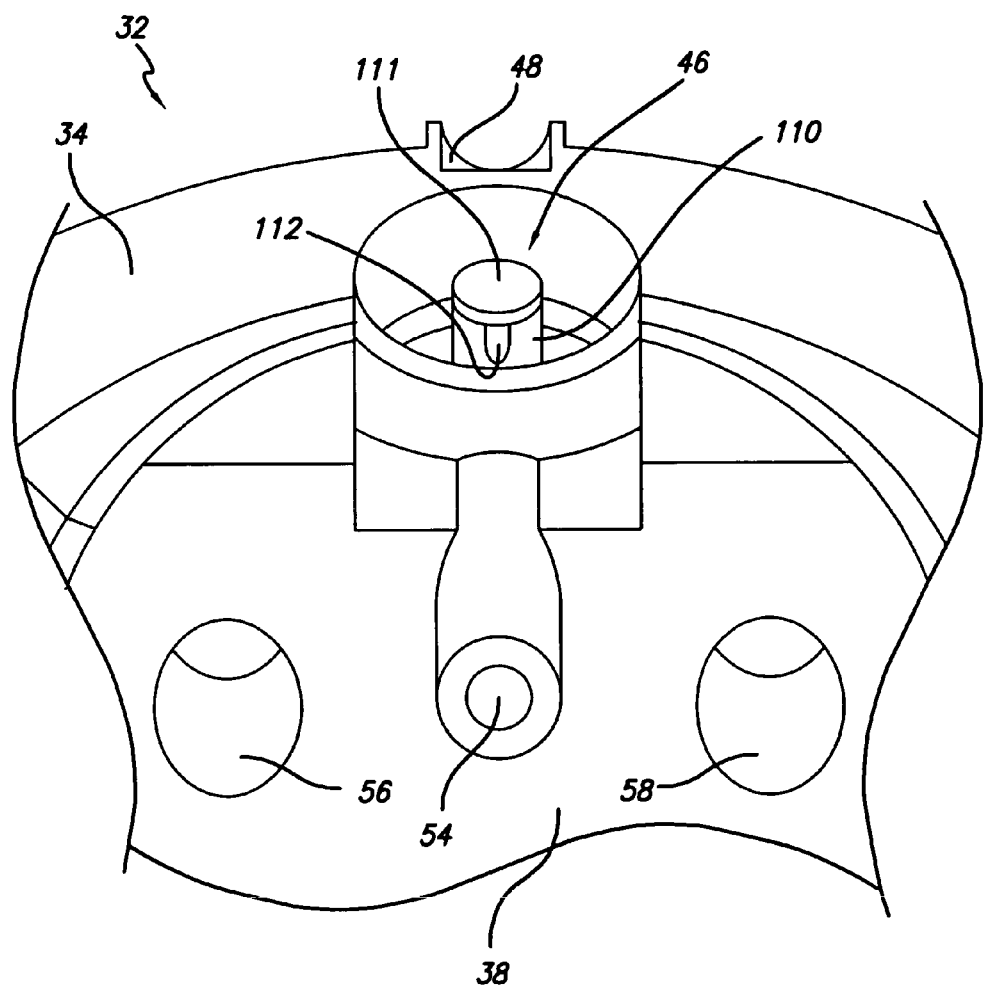
FIG. 20 is a rear perspective detail showing the upper portion of the waste collection cartridge of the invention in isolation.

As best illustrated in FIG. 20, the waste collection cartridge 32 is also equipped with a wand supply port 54, a wand return port 56, and an air discharge port 58 defined as sunken cylindrical sockets in the back wall 38 of the waste collection cartridge 32. The waste collection cartridge 32 also defines internally within its structure a hollow waste collection chamber 62 and a laterally enclosed grit entrainment passageway 60. The grit entrainment passageway 60 is illustrated in FIG. 22 and leads from the air intake 48 to the wand supply port 54.

As illustrated in FIG. 22, the cylindrical grit entrainment duct 60 is formed integrally with the waste collection cartridge 32 and forms a passageway leading from air intake port 48 and from the grit supply coupling 46 to the wand supply port 54. The grit entrainment duct 60 is formed by a plastic tube 61 that is integrally molded with and formed entirely within the structure of the waste collection cartridge 32. The grit entrainment duct 60 is pneumatically isolated from the waste discharge cavity 62 beneath it within the waste collection cartridge 32.

The portable microderm abrasion device 10 also has a movable wand 64, illustrated in FIG. 12, that terminates in a grit dispensing and retrieval tip 66 that is remote from the housing 12. The wand 64 is comprised of a grit supply hose 78 and a separate waste return hose 80. Within the structure of the housing 12 there is a grit supply tube 68 and a separate waste return tube 70, shown in FIG. 10, both of which lead to the grit dispensing and retrieval tip 66. The grit supply tube 68 and the waste return tube 70 are both located entirely within the housing 12 and terminate at a wand interface 76.

The housing 12 has a top end 122 with a wand storage pocket 124 defined therein. The wand storage pocket 124 is visible in FIG. 12 and has a lower surface bounded by the wand storage pocket floor 74. The wand storage pocket 124 is further comprised of a hollow wand interface coupling indicated at 76. The exterior of the interface coupling 76 is visible in FIGS. 11 and 12. The grit supply and waste return tubes 68 and 70 are routed internally within the housing 12 and are coupled to nipples on the interior of the interface coupling 76 located at the rear of the wand pocket storage floor 74.

The interface coupling 76 also has outwardly projecting hose coupling nipples 77 to which the flexible grit supply hose 78 and a grit return hose 80 are secured. The wand 64 is not shown in FIG. 11 to allow illustration of the external hose coupling nipples 77. The proximal ends of the hoses 78 and 80 are secured to the external nipples 77 at the wand interface coupling 76, while the distal ends of the hoses 78 and 80 are secured to nipples 82 and 84 within the structure of the grit dispensing and retrieval tip 66, shown in FIG. 13. The grit supply hose 78 is secured to the grit ejection nipple 82 within the grit dispensing and retrieval tip 66, while the waste return hose 80 is secured to the waste return nipple 84 within the grit dispensing and retrieval tip 66.

Because the hoses 78 and 80 are flexible, they can be coiled in loops so that the entire wand 66 will fit into and can be stored in the wand storage pocket 124. The housing 12 is provided with a releaseable cover 126 for confining the wand 64 in the wand storage pocket 124, as illustrated in FIGS. 1 and 7, for example.

Figure 24:
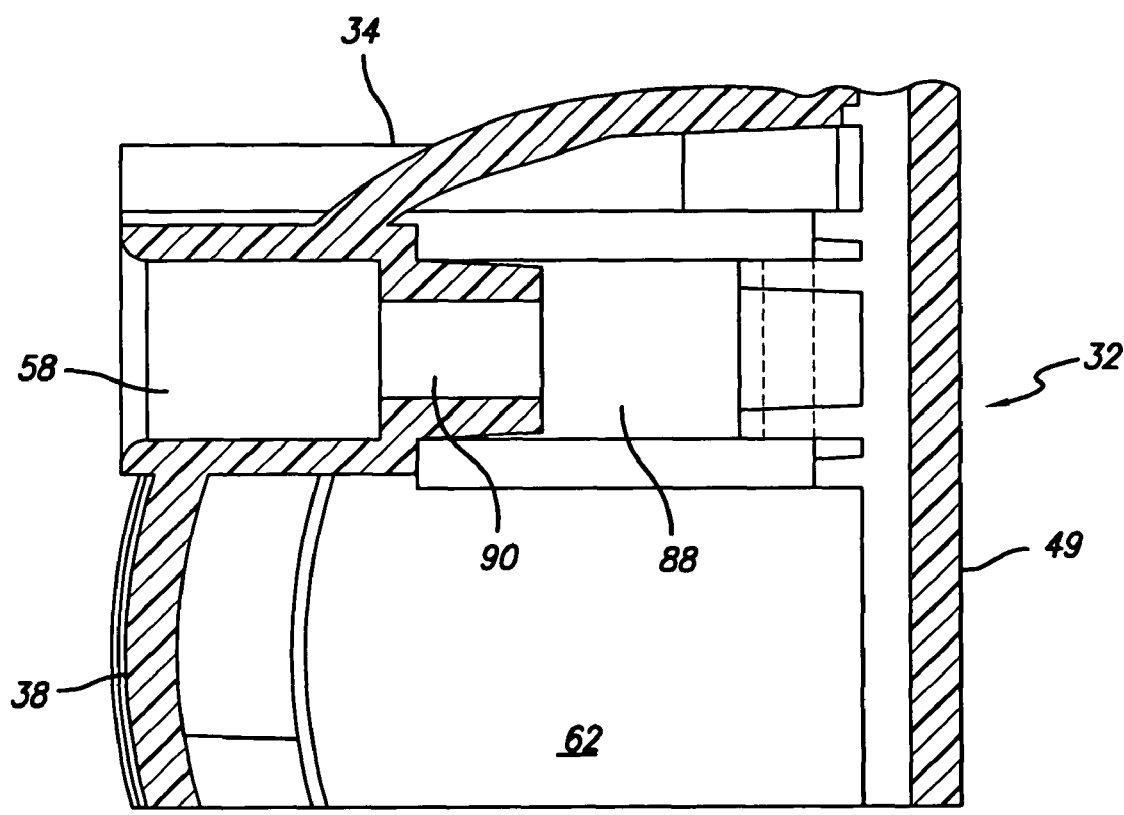
FIG. 24 is a sectional elevational detail illustrating the particle filter located in the waste collection cartridge at the air discharge port thereof.

As illustrated in FIG. 24, a particulate filter 88 is located within the confines of the waste collection cartridge 32. The grit filter 88 is interposed between the wand return port 56 and the air discharge port 58 to exclude grit and exfoliated skin particles from the air discharge port 58. In the embodiment shown, the grit filter 88 is configured as a porous cap on a hollow cylindrical plastic tube 90 that has its outlet at the air discharge port 58.

As illustrated in FIG. 10, an air exhaust tube 92 is connected between the air discharge port 58 and a short cylindrical inlet pipe at the air suction port 18 of the air pump 16. In the embodiment of the invention illustrated the air exhaust tube 92 is interrupted by a T-connection 94, shown in FIG. 10, which also receives a hollow branch line tube at its coupling 96. The branch line tube is located within the housing 12 and leads to a vacuum adjustment valve 98, shown in FIGS. 11 and 12. Rotation of the dial on the valve 98 partially opens or closes a vacuum relief port within the vacuum adjustment valve 98 to allow the user to increase or decrease the suction of the vacuum applied by the grit dispensing and retrieval tip 66.

Figure 16:
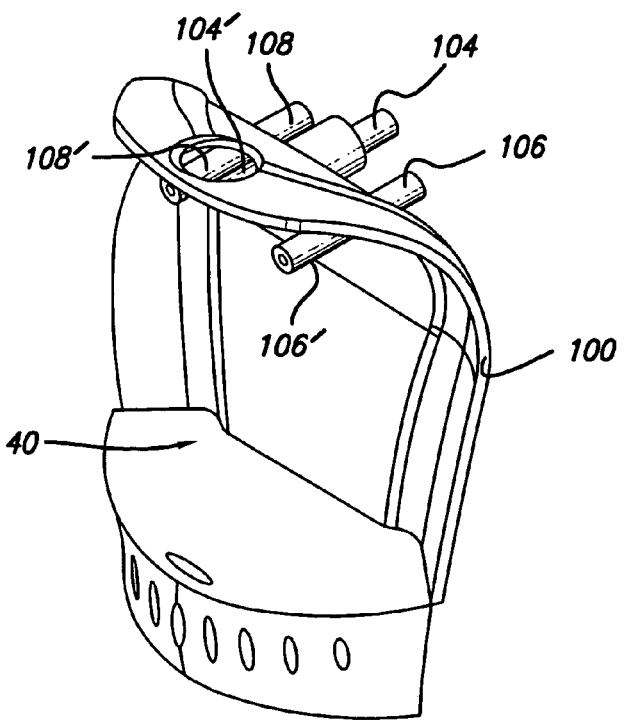
FIG. 16 is a perspective view, partially broken away, of a portion of the housing of the unit of the invention, showing the waste collection cartridge bay and the coupling connections for the waste collection cartridge in isolation.
Figure 17:
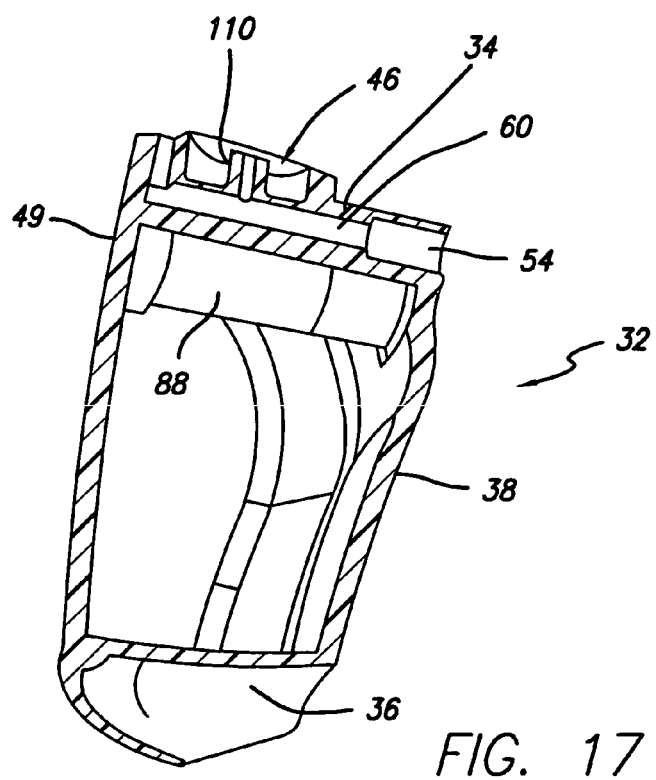
FIG. 17 is a sectional perspective view showing the interior of the waste collection cartridge.

On the front of the housing 12 there is a partition 100 which forms the outwardly facing, concave surface of the waste collection cartridge bay 40. The partition 100 is shown in FIG. 16. Separate hollow cylindrical fittings 104, 106, and 108 are defined on the opposite inside surface of the partition 100 and extend rearwardly toward the hollow interior enclosure of the housing 12. The fitting 104 is a wand supply coupling to which the grit supply tube 68 is connected. The fitting 106 is a wand return coupling to which the waste return tube 70 is connecting. The fitting 108 is an air exhaust coupling to which the air exhaust tube 92 shown in FIG. 10 is connected.

On the outside of the partition 100 corresponding waste collector coupling fittings 104', 106', and 108' project forwardly into the upper region of the waste collection cartridge bay 40. These waste collection coupling fittings are illustrated in FIGS. 16 and 18. As illustrated in FIG. 20, the wand supply port 54, the wand return port 56, and the air discharge port 58 are all configured as interface sockets with openings therein in the back wall 38 of the waste collection cartridge 32. These interface sockets forming the ports 54, 56, and 58 respectively receive the fittings 104', 106', and 108' on the partition 100 in pneumatically sealed engagement therewith.

As illustrated in FIGS. 15, 20, 21 and 22, the grit supply coupling 46 in the top 34 of the waste collection cartridge is formed as a socket that receives the lower extremity of the grit discharge neck 30 of the grit supply cartridge 24 therewithin. The grit supply coupling 46 has a small, upwardly projecting, cylindrical post 110, shown in section in FIG. 21. The post 110 has a flat top but is small enough so that it pierces the septum 28 when the waste collection cartridge 32 is seated in the waste collection cartridge bay 40 and as the grit supply cartridge 24 is inserted into and seated in the grit supply cartridge bay 42.

Figure 21:
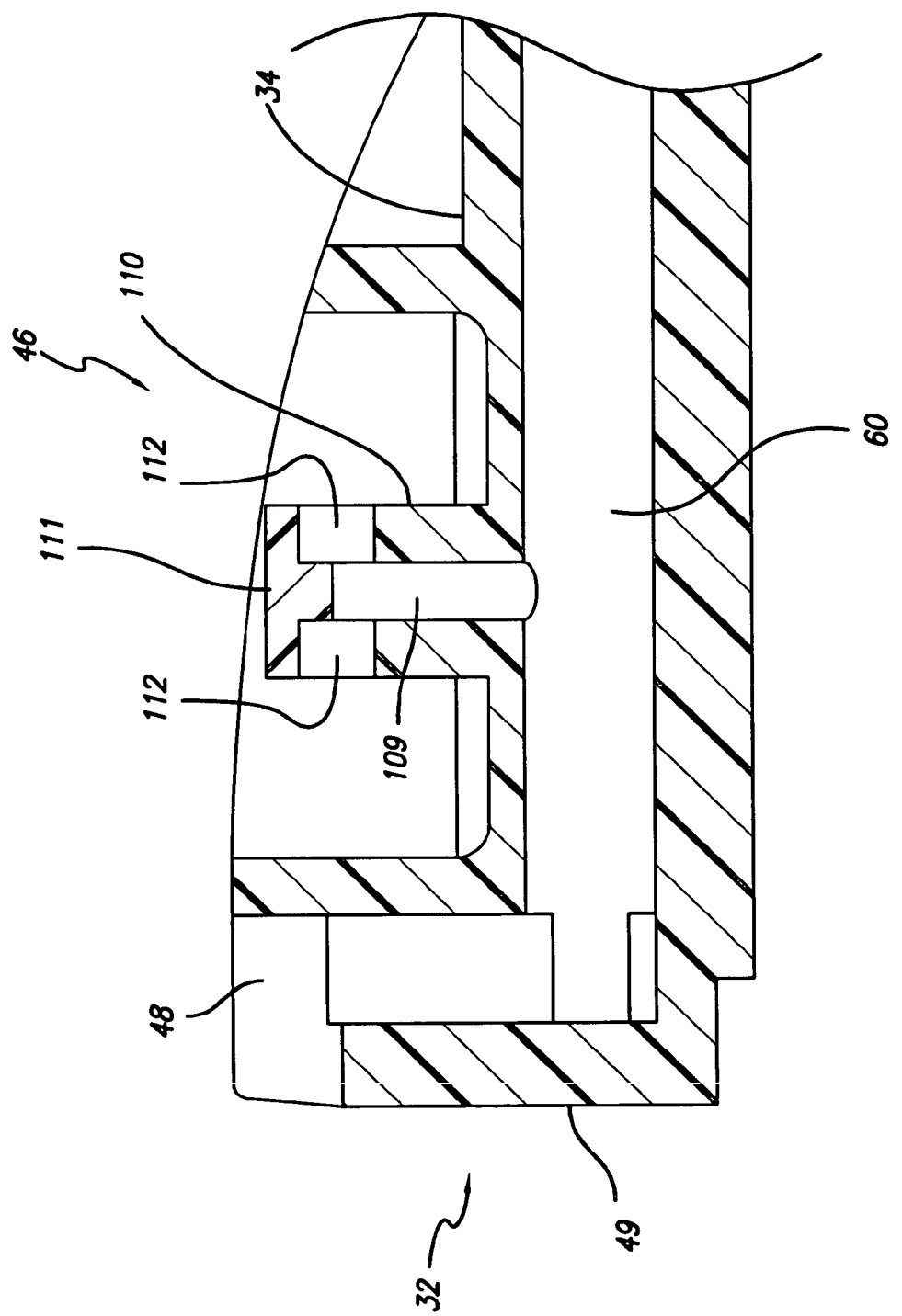
FIG. 21 is a sectional elevational detail of the top of the waste collection cartridge of the invention, shown in isolation, and illustrating the grit entrainment passageway and air intake port.

The upwardly projecting post 110 in the grit supply coupling 46 is hollow with at least one, and preferably a pair, of diametrically opposed, radially oriented openings 112 therein, as shown in FIG. 21. The hollow, cylindrical passage 109 formed within the upwardly projecting post 110 thereby admits grit descending from the grit supply cartridge 24. The grit entrainment passageway 60 intersects the interior passage 109 of the hollow, upwardly projecting post 110 in the grit supply coupling 46. The hollow center passage 109 of the post 110 is in open communication with both the air intake port 48 and the wand supply port 54 of the waste collection cartridge 32.

Figure 23:
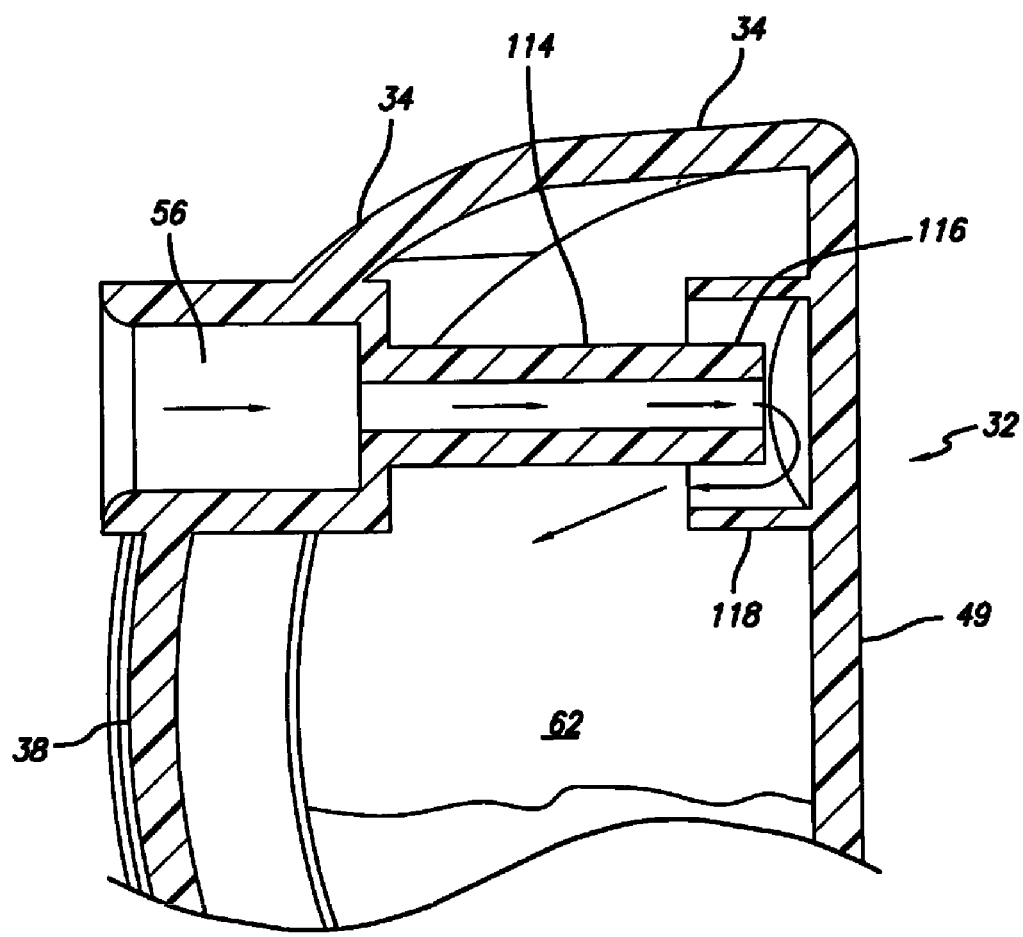
FIG. 23 is a sectional elevational detail illustrating the wand return port in the upper portion of the waste collection cartridge of the invention.

A waste return pipe 114 is defined internally within the structure of the waste collection cartridge 32. The waste return pipe 114 extends from the back wall 38 toward the front wall 49 of the waste collection cartridge 32, as illustrated in FIG. 23. The waste return pipe 114 extends inwardly from the wand return port 56 and terminates just behind the front wall 49. The return pipe 114 has an open waste ejection end 116 terminating in spaced separation from the interior surface of the front wall 49.

As illustrated in FIG. 23, the waste collection cartridge 32 also has an internal, cylindrical, annular waste deflection ring 118 projecting inwardly on the interior surface of the waste collection cartridge front wall 49. The annular waste deflection ring 118 is disposed coaxially about the grit ejection end 116 of the waste return pipe 114.

As illustrated in FIG. 24, the waste collection cartridge 32 has a hollow, cylindrical air exhaust tube 90 defined internally therewithin. The air exhaust tube 90 extends inwardly from the back wall 38 of the hollow waste collection cartridge 32 from the air discharge port 58. A porous grit filter 88 is provided in the form of a cap on the interior end of the air exhaust tube 90. The porous filter cap 88 allows the passage of air from within the waste collection cavity 62 to the air exhaust port 58, but precludes the passage of grit and exfoliated skin therethrough.

FIG. 20 illustrates the upper rear portion of the waste collection cartridge 32 and shows the wand supply port 54, the wand return port 56, and the air discharge port 58 on the back side 38 of the waste collection cartridge 32. The external fittings 104' 106', and 108' at the upper end of the interface partition 100 connect the air/crystal mixture coming from the grit supply crystal cartridge 24 to the tubing and hoses that deliver the mixture to and return the waste from the application wand 64. When the waste collection cartridge 32 is inserted into the receptacle bay 40 in the machine housing 12, the male fittings 104', 106', and 108' insert respectively into the female sockets 54, 56, and 58 in the back side 38 of the waste collection cartridge 32. More specifically, the wand supply port 54 is connected to the wand 64 through the wand grit supply tube 68 and the grit supply hose 78. The return hose 80 and return tube 70 lead to the wand return port 56 which leads to the internal waste cavity 62 of the waste collection cartridge 32.

The fitting 108 on the waste collection cartridge bay 40 is connected on one side to the air exhaust tube 92 that is connected to the vacuum pump 14 and the other male fitting 108' is seated with an airtight coupling to the air discharge port 58. The fitting 104 on the interior side of the partition 100 is connected to the wand supply hose 68, while the opposing fitting 104' is connected with an airtight seal into the wand supply port 54 that is connected to the grit entrainment passageway 60.

When the waste collection cartridge 32 is pressed into the waste bay 40, the external interface fittings 104', 106', and 108' are pressed in airtight connections into the wand supply port 54, the wand return port 56, and the air discharge port 58, respectively. FIGS. 1, 2, 10, and 12 all illustrate the waste collection cartridge 32 seated in its bay 40 in this manner.

When the grit supply cartridge 24 is inserted into the grit supply receiving bay 42, as illustrated in FIGS. 12, 18, and 22, for example, the supply cartridge neck 30 is inserted into the channel 44 so that the post 110 of the grit supply coupling 46 punctures the septum 28 at the grit discharge opening 26 of the grit supply cartridge 24. When this occurs the post 110 punctures the septum 28. The septum 28 may be fabricated as either a self-sealing rubber material or a material that is designed for one use only.

In the embodiment illustrated there is cap 111 on the top of the post 110 and the openings 112 are directed laterally. As a result, the crystals descend into the entrainment passageway 60 primarily due to the force of suction generated by the air pump 16. On the other hand, if the top of the post 110 were left open without a cap and it was simply a tube with an upwardly facing, circular opening, the grit would flow down into the entrainment passageway 60 primarily due to the force of gravity. The microderm abrasion device of the invention can be constructed to operation upon either of these gravity or suction feed principals.

Operation

To utilize the microderm abrasion device 10 the cover 126 is removed and the wand 64 is withdrawn from the wand pocket 124. The waste collection cartridge 32 should be checked to make sure that it is not full. The hollow exfoliation waste collection cartridge 32 is inserted into the waste collection cartridge bay 40 in the housing.

A new or refilled grit supply cartridge 24 is then inserted into the grit supply cartridge bay 42. The grit supply cartridge 24 should be filled with a suitable abrasive substance of the type utilized for conventional microderm abrasion systems. The particles of such a substance are often referred to as "crystals". As used herein, the term crystals can apply to any substance that is applied to the skin during a microderm abrasion process. By way of example, the crystals may comprise sodium bicarbonate and/or other suitable substances.

The microderm abrasion device 10 has an OFF/ON toggle switch 130 located on the top of the housing 12. The switch 130 is normally covered by the lid 126, which must be opened for operation of the device 10. The dial of the vacuum regulating valve 98 is then turned to a level at which it will exert a suitable suction when applied to the skin of a subject.

When the toggle switch 130 is ON, electrical current is applied to the electric motor 14 which drives the air pump 16 causing air to be drawn into the air entrainment passageway 60 through the air intake port 48. An air and grit or crystal mixture is created as the crystals from the supply cartridge 24 pass through the grit entrainment passage 60, as illustrated in FIG. 22. The air/crystal mixture flows through the air entrainment passageway 60 in isolation from the waste collection cavity 62. The air with the crystals entrained therein travels through the entrainment passageway 60, and out of the waste collection cartridge 32, through the wand supply port 54. The crystal and air mixture travels through the grit supply tube 68 and through the interface coupling 76 to the grit supply hose 78.

Figure 13:
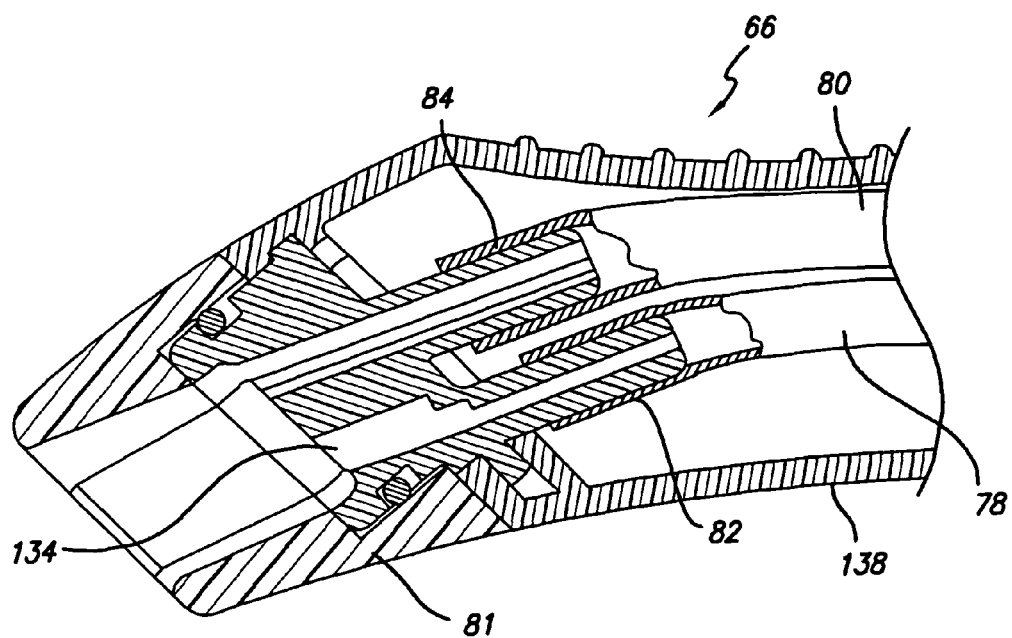
FIG. 13 is a cut away sectional detail view illustrating the interior of the grit dispensing and retrieval tip of the wand of the microderm abrasion unit of the invention.

The grit dispensing and retrieval tip 66 is illustrated in detail in FIG. 13. When the hollow, removable hood 81 of the grit dispensing and retrieval tip 66 is placed against the skin of a subject, a vacuum is created between the grit supply hose 78 and the waste return hose 80. The microderm abrasion crystals are dispensed through the orifice 134 and directed toward, and impact the skin of the subject. Due to the vacuum created within the waste return hose 80 by the hood 81, the used crystals, together with the exfoliated skin loosened by them, are drawn back toward the housing 12 of the microderm abrasion device 10 through the return hose 80.

Before reaching the vacuum pump 16, the mixture of air, spent crystals, and exfoliated skin passes through the waste cavity 62 in the waste collection cartridge 32. However, due to the presence of the filter 88, only the air is drawn out of the exhaust port 58. The spent crystals and skin cells are trapped inside the waste collection cartridge 32 within the waste collection cavity 62. Once the waste cavity 62 becomes full, the entire waste collection cartridge 32 is discarded and replaced.

In manipulating the wand 64 the operator holds the body 138 of the grit dispensing and retrieval tip 66 and presses the opening of the hood 81 thereof against the skin of the subject. The operator slides the hood over the surface of the skin of the subject while maintaining contact between the hood 81 and the skin of the subject. As shown in the sectional view of FIG. 13, the grit dispensing and retrieval tip 66 contains a nozzle orifice 134 which accelerates or changes the air/crystal mixture that is directed against the skin of the subject.

Figure 11:
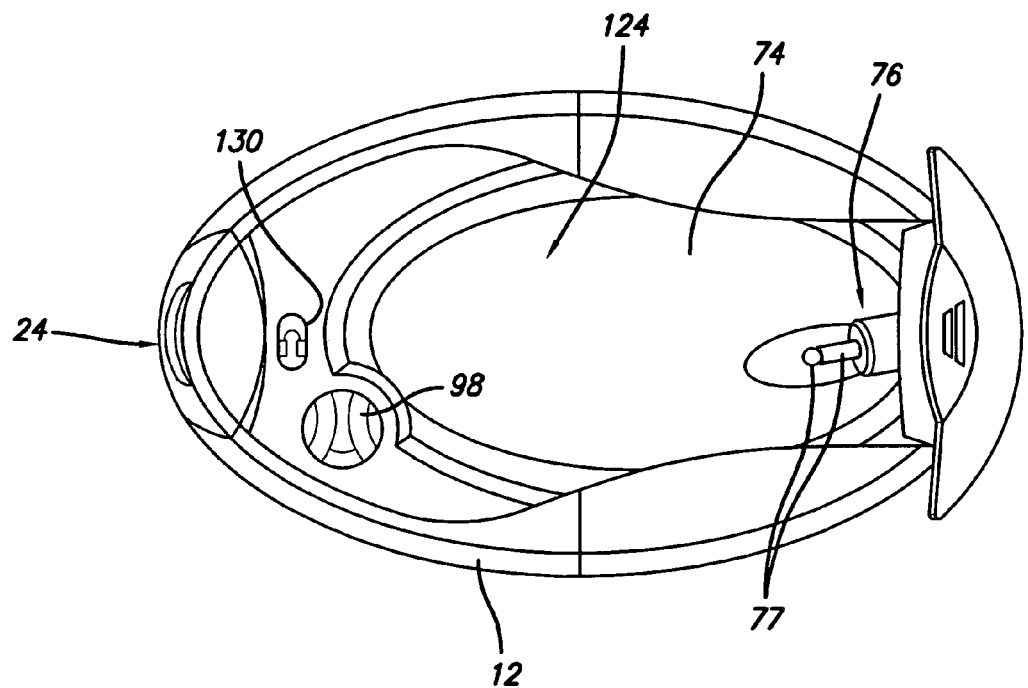
FIG. 11 is a top plan view of the microderm abrasion apparatus shown with the lid for the wand storage cavity thereof removed.

FIGS. 11 and 12 illustrate the wand storage pocket 124 in which the coiled wand hoses 78 and 80 and the grit dispensing and retrieval tip 66 are stored when the unit is not in use. FIGS. 11 and 12 also illustrate the power switch 130 which completes the electrical circuit to turn on the air pump 16. The vacuum adjustment valve 98 which regulates the negative pressure of vacuum that is applied to the grit dispensing and retrieval tip 66 is also illustrated. The adjustment valve 98 regulates a bleed of air into the air exhaust tube 92, which affects the suction throughout the entire system.

When the microderm abrasion 10 is in use and the vacuum pump 16 is turned on with the waste collection cartridge 32 and the grit supply cartridge 24 seated in position as illustrated in FIGS. 1 and 10, the negative pressure created by the air pump 16 in the air exhaust tube 92 causes a flow of air into the air intake port 48 in the waste collection cartridge 32. The negative pressure created in the grit entrainment passageway 60 sucks in particulates of crystal grit through the openings 112 in the center post 110 of the grit supply coupling 46. The crystal grit particles pass down the center passage 109 of the center post 110 and into the grit entrainment passageway 60, then out of the waste collection cartridge 32 through the wand supply port 54. From there the entrained grit is drawn by the vacuum pressure created by the air pump 16 through the wand 64 where it is ejected from the grit dispensing and retrieval tip 66 through the dispensing port 134 shown in FIG. 13. The velocity and density of the air mixture with the grit changes as the grit passes from the narrow grit supply hose 78 into the wider grit discharge opening 134. The air and grit mixture then impacts upon the skin of the subject against which the open mouth of the hood 81 of the grit dispensing and retrieval tip 66 is pressed.

The impact of the grit crystals upon the skin of the subject dislodges particles of dead skin. The air/crystal/skin mixture is laterally confined by the hood 81 and is then drawn into the waste return hose 80 that terminates in the grit dispensing and retrieval tip 66. This waste mixture travels back to the waste collection cartridge 32 from the waste return hose 80 to the waste return tube 70 and reenters the waste collection cartridge 32 through the wand return port 56. The waste mixture is directed through the return tube 114, where turbulence is created at the discharge of the waste from the ejection end 116 thereof due to the annular deflection ring 118. With the reduction in velocity, the grit and skin particles tend fall to the bottom of waste collection chamber 62.

The air is drawn out of the waste collection cartridge 32 by the negative pressure at the air discharge port 58. The air is drawn through the porous filter 88, the very tiny channels of which are too small to allow passage of the grit crystals and skin particles. Therefore, that solid waste material remains in the waste collection chamber 62. The air, on the other hand passes through the porous filter 88 and out through the tube 90 to exit the waste collection cartridge 32 through the air exhaust port 58. The air is drawn through the air exhaust tube 92 and is expelled to the ambient atmosphere by the air pump 16. Because the porous filter 88 prevents grit and skin particles from leaving the waste collection cartridge 32, those solid particles are separated from the air flow and trapped in the waste collection chamber 62.

The portable microderm abrasion device 10 has several important safety features which prevent overtreatment by limiting the abrasive action of the crystals of grit on the skin of the subject. These safety features include, but are not limited to, reducing or cutting off (a) the quantity of crystals that reach the skin; (b) reducing the duration during which the skin is exposed to impacting crystals; (c) reducing the velocity at which the grit crystals impact the skin; and (d) providing a visual, tactile, or audible warning system that cautions the user to stop or reduce treatment. In all or some of the ways of limiting the abrasive action of action on the skin, various sensors can perform certain measurements. Specifically sensors can measure the time a particular area of skin has been exposed to the abrasive media by measuring the movement of the grit dispensing and retrieval tip 66 across the skin of the subject. In addition or alternatively, sensors can measure the time duration of an air flow created between the application wand grit dispensing and retrieval tip 66 and the vacuum source.

Figure 25:
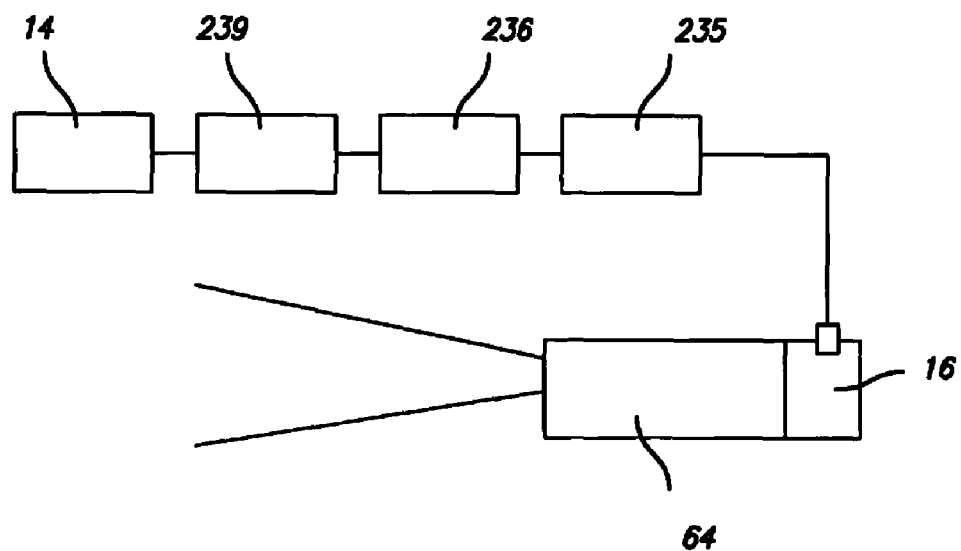
FIG. 25 is a block diagram illustrating a safety system for halting suction after a predetermined period of time by switching off the electric motor in the microderm abrasion device of the invention.

FIG. 25 illustrates a safety feature of the invention that employs a vacuum sensor 235 and a timer 236 coupled to the vacuum source, namely the air pump 16. The vacuum sensor 235 and the timer 236 limit the duration of continuous application of vacuum suction by the vacuum pump 16 upon the grit dispensing and recovery tip 66. When the timer 236 times out, it provides an actuating signal to open an electrical switch 239 that cuts off the flow of electrical power to the motor 14 that operates the air pump 16. In this arrangement, when air flow or vacuum begins anywhere in the system between the wand 64 and the vacuum source, which is the air pump 16, it is sensed by the sensor 235. The sensor 235 in turn actuates the timer 236. Any suitable timer may be utilized. For example, a conventional Tyco Electronics part #2122A4GS timer delay relay may employed as the timer 236. This device turns on after a set amount of time. Alternatively, a Siemens CL-Cu compact time relay may be employed. An Airtrol Components, Inc. Model No. F-4200-X series vacuum switch may be employed as the sensor 235. A Tyco Electronics part #2122AH2SG timer delay relay may be employed as the electrical switch 239. This switch cuts electrical power after a predetermined period time. A Snaptite Miniature wattimizer solenoid valve may be used as the air valve 238.

Figure 26:
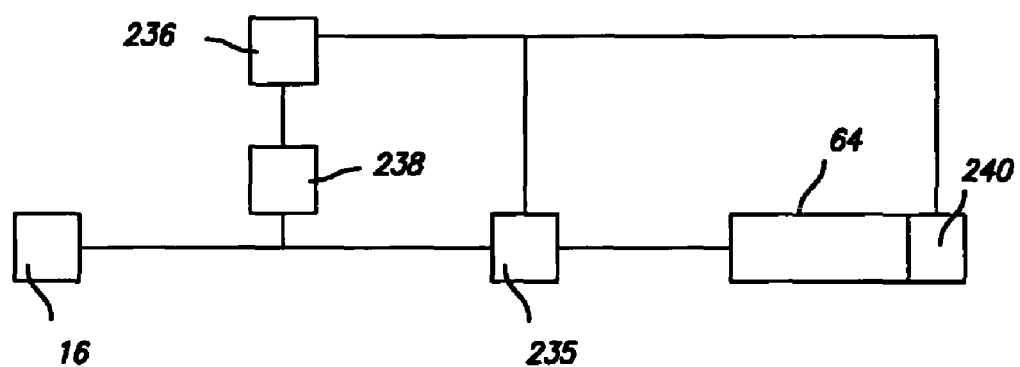
FIG. 26 is a block diagram showing a safety arrangement for halting suction after a predetermined period of time of application of a vacuum by opening the suction line.

FIG. 26 illustrates an alternative arrangement for limiting the abrasive action of crystals on the skin of the subject. This system includes a mechanical or electrical mechanism to stop the air flow to the wand 66. The disruption in air flow can be created anywhere within the entire vacuum line commencing at the air intake port 48 and terminating at the air pump 16. In this arrangement, when air flow through wand 64 due to vacuum begins anywhere in the system, it is sensed by vacuum sensor 235 which in turn actuates a timer 236.

This system also employs a motion sensor 240 in the grit dispensing and recovery tip 66. Whenever the grit dispensing and recovery tip 66 is moved, the motion sensor 240 generates a signal that resets the timer 236. If air flow or vacuum does not cease or significantly decrease during the preset period of time, or if the wand is not kept in relative motion against the skin as determined by a motion sensor 240, an air valve 238 is opened, thus breaking the vacuum and cutting the flow of air to the wand 64. The air pump 16 continues to operate, but vacuum is not created in the wand 64 due to the open line at the air valve 238. The motion sensor 240 located in the grit dispensing and recovery tip 66, and the timer 236 together limit the duration of continuous static application of suction by the vacuum pump 16 at the grit dispensing and recovery tip 66. Upon detection from the motion sensor 240 of a static condition of the grit dispensing and recovery tip 66 for a predetermined duration of time, the timer 236 is actuated. However, if the timer 236 times out suction in the wand 64 is disrupted. Movement detected by the motion sensor 240 resets the timer 235.

Figure 27:
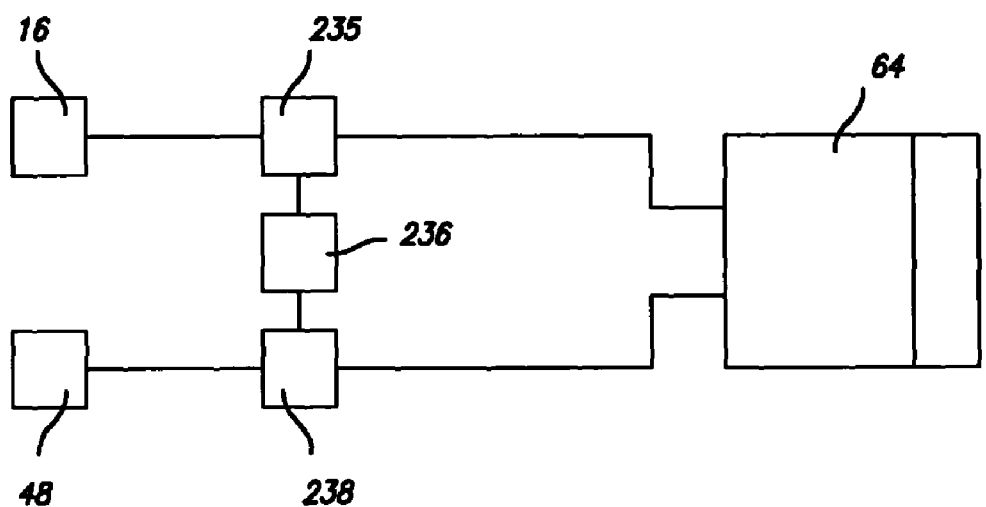
FIG. 27 is a block diagram of another safety arrangement for reducing or halting suction after a predetermined period of time of application of a vacuum.

FIG. 27 illustrates another manner of limiting the abrasive action on the skin of crystals. In this arrangement an actuator, either mechanical, electrical, or other type, changes the density of the mixture or flow of crystals that reach the skin. When the vacuum pump 16 creates an air flow in the system, a vacuum sensor 235 anywhere between the air intake port 48 and the air pump 16 actuates a timer 236. If the air flow or vacuum does not cease or decrease significantly before the timer 236 times out, a vacuum switch, a vacuum regulator, or air valve 238 reduces or cuts off the air flow or vacuum in the abrasive delivery line between the air intake port 48 and the pump 16. Alternatively, the air valve 238 could be replaced with a movable plug or cap that prevents the flow of crystals into the ports 112 in the center post 110 of the grit supply coupling 46.

Figure 28:
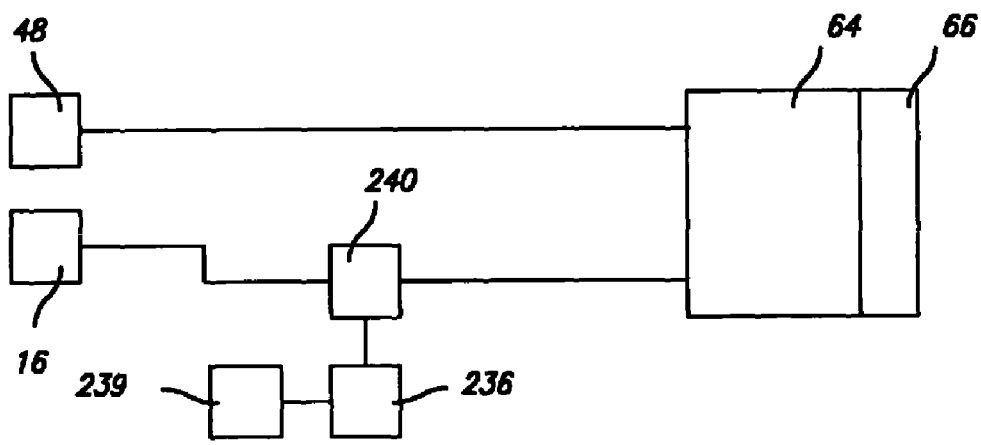
FIG. 28 is a block diagram illustrating removal of the suction when the grit dispensing and retrieval tip remains static for a predetermined period of time.

FIG. 28 illustrates another alternative arrangement in which the delivery of the abrasive crystals is reduced or stopped when the grit dispensing and retrieval tip 66 on wand 64 is not kept in constant motion relative to the skin of the subject. In this arrangement the motion sensor 240 may be either a roller sensor or optical infrared sensor of the type employed in a mouse for a computer, although much smaller. The motion sensor 240 measures movement of the grit dispensing and retrieval tip 66 relative to the skin of the subject. Each time the motion sensor 240 detects movement, it resets a timer 236. When the motion sensor 240 is static, the timer 236 counts up to a predetermined duration of time. Once this time duration is reached, the timer 236 actuates an electrical power switch 239 to cut electrical current to the electrical motor 14. Since the motor 14 no longer operates the air pump 16, the vacuum in the line between the air pump 16 and the air intake port 48 returns to ambient pressure.

Undoubtedly, numerous variations and modifications of the invention will become readily apparent to those familiar with microderm abrasion systems. Accordingly, the scope of the invention should not be construed as limited to the specific embodiments and modifications thereof described and illustrated, but rather is defined in the claims appended hereto.

We claim:

1. A portable microderm abrasion device comprising:
   a hollow housing,
   an electrically operated motor located within said housing,
   an air pump located within said housing and operated by said motor and having an air suction port and an air exhaust port,
   a hollow exfoliation grit supply cartridge removably located in said housing and having a grit discharge opening, said grit supply cartridge being removable from and replaceable in said housing,
   a hollow exfoliation waste collection cartridge separate from said grit supply cartridge and also located in said housing and being removable from and replaceable in said housing independently of said grit supply cartridge, wherein said waste collection cartridge has a grit supply coupling, an air intake port, a wand supply port, a wand return port, and an air discharge port, wherein said grit discharge opening of said grit supply cartridge resides in contact with said grit supply coupling, said grit supply cartridge emptying into said waste collection cartridge,
   a grit entrainment duct defined within said waste collection cartridge and leading from said air intake port and from said grit supply coupling and to said wand supply port, said grit entrainment duct being integrally molded with and formed entirely within said waste collection cartridge, said grit entrainment duct being pneumatically isolated from a waste discharge cavity within said waste collection cartridge,
   a movable wand terminating in a grit dispensing and retrieval tip remote from said housing,
   separate exfoliation grit supply and waste return tubes leading to said grit dispensing and retrieval tip, wherein said exfoliation grit supply tube is coupled between said grit dispensing and retrieval tip and said wand supply port, and said waste return tube is coupled between said grit dispensing and retrieval tip and said wand return port,
   a grit filter located in said waste collection cartridge and interposed between said wand return port and said air discharge port to exclude particulate matter from said air discharge port, and
   an air exhaust tube connected between said air discharge port and said air suction port.

2. A device according to claim 1 wherein said hollow housing has an outer surface defining an exposed grit supply cartridge bay for receiving and seating said grit supply cartridge and a separate exposed waste collection cartridge bay for receiving and seating said waste collection cartridge, and an enclosed channel is defined in said housing between said grit supply and waste collection cartridge bays, to accommodate communication between said grit discharge opening of said grit supply cartridge and said grit supply coupling of said waste collection cartridge when said grit supply and waste collection cartridges are seated in their respective bays.

3. A device according to claim 2 wherein said grit supply cartridge has upper and lower ends and said grit supply cartridge is configured with a narrow grit discharge neck terminating in said grit discharge opening in said lower end thereof.

4. A device according to claim 2 wherein said grit discharge opening is covered by a puncturable septum and said waste collection cartridge has upper and lower ends and said grit supply coupling is formed in said upper end of said waste collection cartridge as a socket that received said grit discharge neck snugly therewithin and an upwardly projecting post centered in said socket that pierces said septum when said waste collection cartridge is seated in said waste collection cartridge cavity and as said grip supply cartridge is inserted into and seated in said grit supply cartridge cavity.

5. A device according to claim 4 wherein said upwardly projecting post is hollow and in open communication with said air intake port and with said wand supply port of said waste collection cartridge and said upwardly projecting post has at least one opening therein.

6. A device according to claim 5 wherein said waste collection cartridge defines a grit collection chamber and has a laterally enclosed passageway defined within the structure of said waste collection cartridge and isolated from said waste collection chamber and leading from said air intake port to said wand supply port and intersecting the interior of said hollow upwardly projecting post in said grit supply coupling.

7. A device according to claim 6 wherein said hollow post is cylindrical and has a closed top and said at least one opening therein is a radial flow port.

8. A device according to claim 2 wherein said waste collection cartridge has upper and lower ends and an inside wall facing said waste collection cartridge bay in said housing, and said housing has a partition forming a surface of said grit collection cartridge bay, and separate hollow nipples are defined on said partition and extending into said grit collection cartridge bay, including a wand supply nipple, a wand return nipple, and an air exhaust nipple, and said wand supply port, said wand return port and said air discharge ports are all defined as interface sockets with openings therein in said inside wall of said waste collection cartridge and said interface sockets releaseably receive said nipples on said partition in pneumatically sealed engagement therewith.

9. A device according to claim 1 wherein said grit collection cartridge has an air exhaust tube defined therewithin and extending inwardly within the confines of said hollow waste collection cartridge from said air discharge port, and said grit filter is comprised of a porous plug in said air exhaust tube, wherein said porous plug permits the passage of air therethrough and precludes the passage of grit therethrough.

10. A device according to claim 1 wherein said housing has a top end with a wand storage pocket having a wand storage pocket floor defined therein and further comprising a hollow wand interface between said wand and said grit supply and waste return tubes wherein said grit supply and waste return tubes are located entirely within said housing and terminate at said wand interface, and said wand is further comprised of separate flexible grit supply and waste return hoses that are coupled to said wand interface and to said grit dispensing and retrieval tip, whereby said hoses can be coiled and said wand stored in said wand storage pocket.

11. A device according to claim 10 further comprising a releaseable cover on said housing for confining said wand in said wand storage pocket.

12. A device according to claim 1 further comprising a manually operable switch on said housing for selectively increasing and decreasing suction force exerted by said air pump.

13. A device according to claim 1 wherein said waste collection cartridge has a front wall and a waste return pipe defined within said waste collection cartridge extending inwardly from said wand return port and directed toward said front wall and having a grit ejection end terminating in spaced separation from said front wall.

14. A device according to claim 13 further comprising an annular waste deflection ring projecting inwardly from said front wall and disposed coaxially about said grit ejection end of said waste return pipe.

15. In a microderm abrasion apparatus having a housing containing an electric motor, a pneumatic vacuum pump, a wand movable relative to said housing and having a grit dispensing and recovery tip, the improvement comprising a disposable abrasive waste recovery cartridge seated in said housing, a separate disposable grit supply cartridge seated in said housing and also upon said disposable abrasive waste recovery cartridge, said grit supply cartridge emptying into said waste recovery cartridge through a grit supply coupling on said waste recovery cartridge, and a grit entrainment duct defined within said waste recovery cartridge, said grit entrainment duct being integrally molded with and formed entirely within said waste recovery cartridge, whereby said grit supply cartridge and said waste recovery cartridge are detachable from said housing separately from each other, a vacuum sensor, a timer coupled to said vacuum sensor for measuring the duration of continuous application of vacuum suction by said vacuum pump upon said grit dispensing and recovery tip, and means for interrupting the supply of grit to said grit dispensing and recovery tip in response to signals from said timer.

16. A device according to claim 15 wherein said means for interrupting said supply of grit is a vacuum interruption valve located between said disposable grit supply cartridge and said vacuum pump.

17. A device according to claim 15 wherein said means for interrupting said supply of grit is an electrical power interruption switch connected to said electric motor.

18. A device according to claim 15 wherein said means for interrupting said supply of grit is a mechanism for blocking the flow of grit to said grit dispensing and recovery tip.

19. In a microderm abrasion apparatus having a housing containing an electric motor, a pneumatic vacuum pump, a wand movable relative to said housing and having a grit dispensing and recovery tip, the improvement comprising a disposable abrasive waste recovery cartridge seated in said housing, a separate disposable grit supply cartridge seated in said housing and also upon said disposable abrasive waste recovery cartridge, said grit supply cartridge emptying into said waste recovery cartridge through a grit supply coupling on said waste recovery cartridge, and a grit entrainment duct defined within said waste recovery cartridge, said grit entrainment duct being integrally molded with and formed entirely within said waste recovery cartridge, whereby said grit supply cartridge and said waste recovery cartridge are detachable from said housing separately from each other, further comprising a vacuum sensor, a timer coupled to said vacuum sensor, and a flow check device connected to said timer and to said grit supply cartridge to block the flow of grit therefrom upon duration of said vacuum for a predetermined time interval.

20. A microderm abrasion apparatus according to claim 19 further comprising a motion sensor in said grit dispensing and recovery tip and a timer for limiting the duration of continuous application of suction by said vacuum pump at said grit dispensing and recovery tip upon detection from said motion sensor of a static condition of said grit dispensing and recovery tip for a predetermined duration of time.

* * * * *